(12) United States Patent  
Chandrasekaran et al.

(10) Patent No.: US 8,883,010 B2
(45) Date of Patent: Nov. 11, 2014

(54) POLYMER COMPOSITION WITH PHYTOCHEMICAL AND DIALYSIS MEMBRANE FORMED FROM THE POLYMER COMPOSITION

(75) Inventors: Neelakandan Chandrasekaran, Woodbury, MN (US); Thein Kyu, Akron, OH (US)

(73) Assignee: The University of Akron, Akron, OH (US)

( * ) Notice: Subject to any disclaimer, the term of this patent is extended or adjusted under 35 U.S.C. 154(b) by 469 days.

(21) Appl. No.: 13/084,696

(22) Filed: Apr. 12, 2011

(65) Prior Publication Data

US 2011/0186518 A1 Aug. 4, 2011

Related U.S. Application Data

(63) Continuation-in-part of application No. PCT/US2009/066166, filed on Dec. 1, 2009.

(60) Provisional application No. 61/324,062, filed on Apr. 14, 2010, provisional application No. 61/119,822, filed on Dec. 4, 2008.

(51) Int. Cl.
| | |
|---|---|
| *B01D 61/24* | (2006.01) |
| *B01D 61/28* | (2006.01) |
| *B01D 71/56* | (2006.01) |
| *B01D 71/68* | (2006.01) |
| *C07D 311/30* | (2006.01) |
| *C07D 311/36* | (2006.01) |
| *C08K 5/1545* | (2006.01) |
| *B01D 71/44* | (2006.01) |
| *A61K 31/35* | (2006.01) |
| *A61K 9/70* | (2006.01) |

(52) U.S. Cl.
CPC ............. *A61K 31/35* (2013.01); *B01D 2323/39* (2013.01); *B01D 71/44* (2013.01); *B01D 61/243* (2013.01); *B01D 2325/48* (2013.01); *B01D 71/68* (2013.01); *B01D 71/56* (2013.01); *A61K 9/7007* (2013.01)

USPC ............ 210/646; 210/321.6; 210/500.23; 210/500.38; 210/500.41; 210/650; 264/178 R; 29/428; 524/110; 549/243

(58) Field of Classification Search
CPC .............. A23V 2250/2116; B01D 2323/39; B01D 2325/48; B01D 61/243; B01D 71/44; B01D 71/56; B01D 71/68; A61K 9/7007; A61K 31/35
USPC ............ 210/646, 500.33, 500.23, 321.6, 650, 210/500.38, 500.41; 524/110; 549/203; 29/428; 264/178 R
See application file for complete search history.

(56) References Cited

U.S. PATENT DOCUMENTS

| 4,456,746 A | 6/1984 | Horner |
| 4,722,795 A | 2/1988 | Gohl et al. |

(Continued)

FOREIGN PATENT DOCUMENTS

EP 0 780 133 3/2000

OTHER PUBLICATIONS

Chemical Handbook, 24937-78-8 (Ethylene-vinyl acetate copolymer) Product Description (2007).*

(Continued)

*Primary Examiner* — John Kim
(74) *Attorney, Agent, or Firm* — Renner Kenner Greive Bobak Taylor & Weber

(57) ABSTRACT

A biocompatible polymer composition which includes a matrix material and at least one of an isoflavone and a flavone at least partially dispersed in the matrix material is suited to use in a membrane for hemodialysis and other in vivo and in vitro applications.

34 Claims, 24 Drawing Sheets

(56) References Cited

U.S. PATENT DOCUMENTS

| | | | |
|---|---|---|---|
| 4,935,141 | A | 6/1990 | Buck et al. |
| 5,152,894 | A | 10/1992 | Haubs et al. |
| 5,505,851 | A | 4/1996 | Wagener et al. |
| 5,911,880 | A | 6/1999 | Klein et al. |
| 6,329,422 | B1* | 12/2001 | Fischer et al. ............... 514/456 |
| 6,382,526 | B1 | 5/2002 | Reneker et al. |
| 6,520,425 | B1 | 2/2003 | Reneker |
| 6,958,156 | B2 | 10/2005 | Hendler et al. |
| 7,320,797 | B2 | 1/2008 | Gupta |
| 2002/0055644 | A1 | 5/2002 | Winter et al. |
| 2002/0055844 | A1 | 5/2002 | L'Esperance et al. |
| 2005/0244647 | A1* | 11/2005 | Droschel et al. ............. 428/412 |
| 2006/0165798 | A1 | 7/2006 | Edgren et al. |
| 2007/0207179 | A1 | 9/2007 | Andersen et al. |
| 2008/0000830 | A1 | 1/2008 | Mabuchi et al. |
| 2008/0142442 | A1* | 6/2008 | Steiger et al. ................ 210/646 |

OTHER PUBLICATIONS

Katsuyama et al., "One-pot synthesis of genistein from tyrosine by coincubation of genetically engineered *Escherichia coli* and *Saccharomyces cerevisiae* cells," Applied Microbiology and Biotechnology vol. 73, No. 5, 1143-1149 (2007)—abstract only.

Bloch, et al. "Position of the American Dietetic Association: Phytochemicals and functional foods," Journal of the American Dietetic Association, Apr. 1995, vol. 95, No. 4.

Miura, et al. "Antidiabetic activity of a xanthone compound, mangiferin," Phytomedicine, vol. 8(2), pp. 85-87, Mar. 2001.

Ratner, et al. "Biomaterials: Where We Have Been and Where We Are Going," Annu. Rev. Biomed. Eng., 2004, 6:41-75.

Tang, et al. "Characterizaton of Antioxidant and Antiglycation Properties and Isolation of Active Ingredients From Traditional Chinese Medicines," Free Radical Biology & Medicine, vol. 36, No. 12, pp. 1575-1587, 2004.

Ward, et al. "What Clinically Important Advances in Understanding and Improving Dialyzer Function Have Occurred Recently?" Seminars in Dialysis, vol. 14, No. 3 May-Jun. 2001, pp. 160-162.

Sasaki, et al. "Development of vitamin E-modified polysulfone membrane dialyzers," J Artif Organs (2006) 9:50-60.

Descamps-Latscha, et al. "Dialysis-Induced Oxidative Stress: Biological Aspects, Clinical Consequences, and Therapy," Seminars in Dialysis, vol. 14, No. 3 May-Jun. 2001, pp. 160-162.

Rodríguez, et al. "Effects of a natural extract from L, and its active compound, mangiferin, on energy state and lipid peroxidation of red blood cells," Biochimica et Biophysica Acta 1760 (2006) 1333-1342.

Chandrasekaran, et al. "Effects of genistein modification on miscibility and hydrogen bonding interactions in poly(amide)/poly(vinyl pyrrolidone) blends and membrane morphology development during coagulation," Polymer 51 (2010) 5135-5144.

Peterson, et al. "Evaluation of the Biochemical Targets of Genistein in Tumor Cells," The Journal of Nutrition, Mar. 1995, v.125(35), p. 784S-789S.

Leiro, et al. "Expression profiles of genes involved in the mouse nuclear factor-kappa B signal transduction pathway are modulated by mangiferin," International Immunopharmacology 4 (2004) 763-778.

Verdrengh, et al. "Genistein as an anti-inflammatory agent," Inflamm. res. 52 (2003) 341-346.

Xu, et al. "Genistein Inhibits Expressions of NADPH Oxidase p22phox and Angiotensin II Type 1 Receptor in Aortic Endothelial Cells from Stroke-Prone Spontaneously Hypertensive Rats," Hypertens Res vol. 27, No. 9 (2004).

Mohanty, et al. "Glucose Challenge Stimulates Reactive Oxygen Species (ROS) Generation by Leucocytes," Journal of Clinical Endocrinology & Metabolism, 2000, 85: 2970-2973.

Parikh, et al. "IL-6 Production in Human Intestinal Epithelial Cells Following Stimulation with IL-1β Is Associated with Activation of the Transcription Factor NF-κB[1]," Journal of Surgical Research, 69, 139-144 (1997).

Kimmel, et al. "Immunologic function and survival in hemodialysis patients," Kidney International, vol. 54, 1998, pp. 236-244.

Leiro, et al. "In vitro effects of mangiferin on superoxide concentrations and expression of the inducible nitric oxide synthase, tumour necrosis factor-α and transforming growth factor-β genes" Biochemical Pharmacology 65 (2003) 1361-1371.

Garrido, et al. "In vivo and in vitro anti-inflammatory activity of *Mangifera indica* L. extract (VIMANG®)," Pharmacological Research 50 (2004) 143-149.

Herbelin, et al. "Influence of uremia and hemodialysis on circulating interleukin-1 and tumor necrosis factor α," Kidney International, vol. 37 (1990), pp. 116-125.

Chandrasekaran, et al. "Miscibility Characterization in Relation to Phase Morphology of Poly(ether sulfone)/Poly(vinyl pyrrolidone) Blends Containing a Phytochemical," J. Phys. Chem. B 2009, 113, 8520-8526.

Chandrasekaran, et al. "Hydrogen bonding interactions and miscibility studies of poly(amide)/poly- (vinyl pyrrolidone) blends containing mangiferin," Polymer 50 (2009) 2885-2892.

Chandrasekaran, et al. "Membrane morphology and phase diagrams of mangiferin modified poly(amide)/poly(vinyl pyrrolidone) blends," Journal of Membrane Science 367 (2011) 240-248.

García, et al. "Modulation of rat macrophage function by the *Mangifera indica* L. extracts Vimang and mangiferin," International Immunopharmacology 2 (2002) 797-806.

Galli, et al. "Oxidant Stress in Hemodialysis," Nephron 2000;84:1-5.

Miesel, et al. "Priming of NADPH Oxidase by Tumor Necrosis Factor Alpha in Patients with Inflammatory and Autoimmune Rheumatic Diseases," Inflammation, vol. 20, No. 4, 1996.

Sánchez, et al. "Protective Effects of *Mangifera indica* L. Extract, Mangiferin and Selected Antioxidants Against TPA-Induced Biomolecules Oxidation and Peritoneal Macrophage Activation in Mice," Pharmacological Research, vol. 42, No. 6, 2000.

Canestrari, et al. "Redox state, antioxidative activity and lipid peroxidation in erythrocytes and plasma of chronic ambulatory peritoneal dialysis patients," Clinica Chimica Acta 234 (1995) 127-136.

Nilsson, et al. "The role of complement in biomaterial-induced inflammation," Molecular Immunology 44 (2007) 82-94.

Hench, et al. "Third-Generation Biomedical Materials," Science 295, 1014 (2002).

Schindler, et al. "Transcription, not synthesis, of interleukin-1 and tumor necrosis factor by complement," Kidney International, vol. 37 (1990), pp. 85-93.

Pinto, et al. "Xanthone Derivatives: New Insights in Biological Activities," Current Medicinal Chemistry, 2005, 12, 2517-2538.

Sarkar, et al. "β-D-Glucoside Suppresses Tumor Necrosis Factor-induced Activation of Nuclear Transcription Factor κB but Potentiates Apoptosis*," The Journal of Biological Chemistry, vol. 279, No. 32, Issue of Aug. 6, pp. 33768-33781, 2004.

Chandrasekaran, et al. "Miscibility Studies on Polymer Blends Modified with Phytochemicals," American Physical Society, Mar. 16-20, 2009—abstract only.

Braune, et al. "Deglycosylation of puerarin and other aromatic C-glucosides by a newly isolated human intestinal bacterium," Environmental Microbiology, vol. 13, Issue 2, pp. 482-494, Feb. 2011—abstract only.

* cited by examiner

100/0 PA/G

90/10 PA/G

80/20 PA/G

70/30 PA/G

50/50 PA/G

100/0 PES/G

90/10 PES/G

POLYMER COMPOSITION WITH PHYTOCHEMICAL AND DIALYSIS MEMBRANE FORMED FROM THE POLYMER COMPOSITION

This application claims the benefit of U.S. application Ser. No. 61/324,062, filed on Apr. 14, 2010, entitled GENISTEIN: A SOYBEAN DERIVED PHYTOCHEMICAL AND ITS APPLICATIONS, by Neelakandan Chandrasekaran and Thein Kyu, and claims the priority, as a continuation-in-part, of International Application PCT/US09/66166, filed Dec. 1, 2009, POLYMER COMPOSITION AND DIALYSIS MEMBRANE FORMED FROM THE POLYMER COMPOSITION by Neelakandan Chandrasekaran and Thein Kyu, and of U.S. application Ser. No. 61/119,822, filed on Dec. 4, 2008, entitled POLYMER COMPOSITION AND DIALYSIS MEMBRANE FORMED FROM THE POLYMER COMPOSITION, by Neelakandan Chandrasekaran and Thein Kyu, from which PCT/US09/66166 claims the benefit, the disclosures of all of which are incorporated herein in their entireties, by reference.

BACKGROUND

The exemplary embodiment relates to a biocompatible polymer composition which includes a phytochemical. In particular, it relates to a biocompatible polymer where the phytochemical is an isoflavone, such as genistein. The polymer composition finds particular application in forming dialysis membranes, and will be described with particular reference thereto. However, it is to be appreciated that the present exemplary embodiment is also amenable to other like applications.

Hemodialysis is used for filtering impurities from the blood, for example, to provide an artificial replacement for lost kidney function. In hemodialysis, patient blood is typically pumped for repeated cycles through a dialyzer unit packed with hollow fiber bundles made-up of hydrophobic/hydrophilic polymer blends to reduce urea and uremic toxin concentration in blood to physiologically acceptable levels. However, there are problems associated with hemodialysis, such as an increase in oxidants in the blood and inflammatory responses due to long term exposure of the blood to a synthetic polymer surface. These complications are referred to as dialysis induced oxidative stress (DIOS), and membrane induced inflammation (MII) in blood and can result in cardiovascular problems and, in some cases, death. In DIOS, excess production of oxygen radicals can overpower the natural antioxidant defense mechanisms of the body. The bioincompatibility of the polymeric hemodialysis membranes has been implicated as the primary source of generation of excessive reactive oxygen species (ROS), which contribute to DIOS. MII causes an immune response resulting from higher concentrations of pro-inflammatory cytokines, such as interleukin-1β (IL-1β) and interleukin (IL-6), and tumor necrosis factor-α (TNF-α). A dialysis patient generally undergoes supplemental drug therapy to counteract these effects. There remains a need for membranes that are capable of suppressing these long term ill-effects.

Surface modification techniques have been employed to produce biocompatible materials which are suited to use in hemodialysis membranes. These include polyethylene glycol grafting, albumin coatings, phospholipid mimicking surfaces, plasma treatments, fluorination, modification using anti-platelet agents like prostacyclin and fibrinolytic agents, and heparinizing the surface. Anti-bacterial surface treatments have also been proposed. However, problems remain.

The exemplary embodiment provides a biocompatible polymer composition suited to use in a hemodialysis membrane which can alleviate some of these problems.

BRIEF DESCRIPTION OF THE DISCLOSURE

In accordance with one aspect of the exemplary embodiment, a biocompatible polymer composition includes a matrix material and at least one of an isoflavone and a flavone, which is at least partially (or entirely) dispersed therein.

In another aspect, a method of forming a dialyzer filter unit includes forming a membrane from the polymer composition, and inserting the membrane into a housing of the dialyzer filter unit.

In another aspect, a method of removing free radicals from a fluid includes filtering a fluid with the membrane, whereby free radicals in the fluid are removed by the above-described membrane.

In another aspect, a method for hemodialysis and/or hemofiltration includes contacting blood with a hollow fiber membrane comprising the biocompatible composition.

In another aspect, a method for forming a polymer composition includes combining a matrix material for forming a polymer matrix and at least one of an isoflavone and a flavone to form a mixture and solidifying the mixture to form the polymer composition.

In another aspect, a biocompatible polymer composition consists essentially of polyvinylpyrrolidone, at least one of a polyamide and a polyethersulfone, and at least one hydroxyisoflavone.

In another aspect, a medical device includes at least one of a hydroxyflavone and a hydroxyisoflavone.

DETAILED DESCRIPTION

Figure 1:
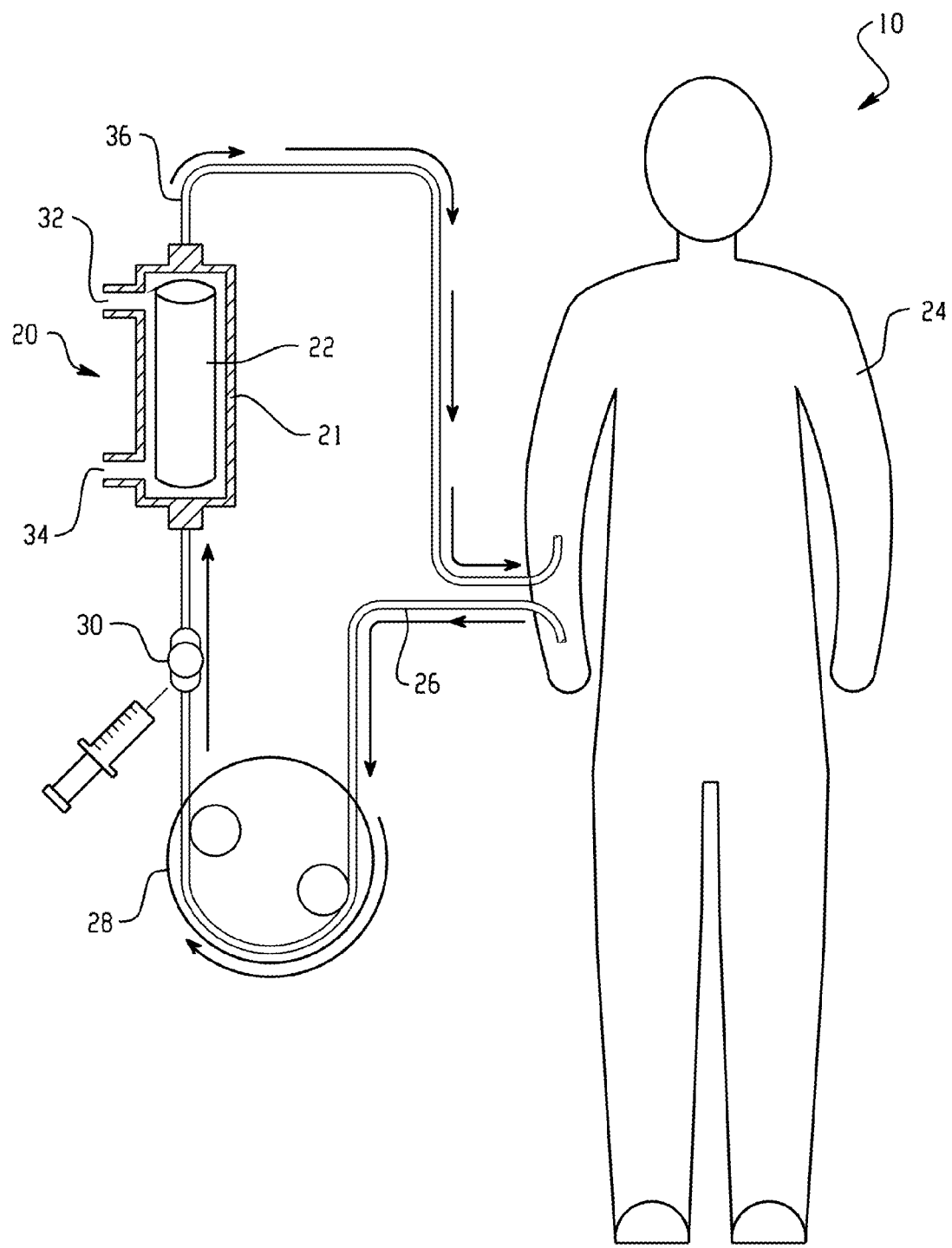
FIG. 1 is a schematic view of a hemodialysis circuit including a dialyzer filter containing an exemplary semi-permeable membrane formed from a biocompatible polymer composition.

Aspects of the exemplary embodiment relate to a biocompatible polymer composition, a membrane formed therefrom, a dialysis filter incorporating the membrane and/or other components formed from the polymer composition, a method of forming membranes from the polymer composition and to a method for reducing free radicals in a liquid, such as blood.

As used herein, the word polymer refers to homopolymers formed from a single monomer as well as copolymers formed from more than one monomer, block copolymers, polymer blends held together by ionic and/or weaker forms of bonding, and functionalized polymers. The polymer composition finds application in hemodialysis, such as in a dialysis membrane, in which the biocompatible polymer composition may act as a scavenger for free radicals and peroxides. The exemplary composition can thus help to reduce dialysis-induced reactive oxidative species (ROS), and lead to reduced concentrations of pro-inflammatory cytokines than with existing membranes such as those formed from Vitamin E-modified polymers.

The exemplary polymer composition is also biocompatible. By "biocompatible" it is meant that the composition is compatible with blood or may perform useful functions within the human body without having toxic or injurious effects.

In various aspects, a functional hemodialysis membrane is disclosed which is modified with one or more of a group of plant-derived chemicals (or synthetic variants thereof) known as phytochemicals. Phytochemicals have widespread availability and low toxicity. By way of example, genistein, a soybean-derived phytochemical, is employed as the modifying agent. It has anti-oxidant and anti-inflammatory properties. It can be combined with a biocompatible polymer suitable for forming membranes.

By way of example, the in vitro effects of genistein modified polymer membranes on cytotoxicity, oxidative burst (i.e., generation of ROS) and cytokine levels in human blood have been studied and demonstrate its effectiveness.

The Biocompatible Polymer Composition

The biocompatible polymer composition includes a polymer matrix material and at least one modification agent, such as an antioxidant, such as a phytochemical, dispersed therein The modification agent can be a flavone or isoflavone, both of which can be antioxidants.

The Modification Agent

By "flavone" or "isoflavone," it is meant an unsubstituted flavone or isoflavone or a substituted derivative thereof. The term (iso)flavone is used to refer to a flavone, isoflavone or combination thereof. The exemplary (iso)flavone in the composition can be an isolated, naturally occurring isoflavone(s), synthesized isoflavone(s), or a combination thereof. In the exemplary embodiment, the flavone or isoflavone may be an hydroxy(iso)flavone (i.e., a hydroxyflavone or hydroxyisoflavone), having at least one hydroxyl group, such as a polyphenol, i.e., a molecule having at least two phenol groups. Although not fully understood, it is believed that the phenol group(s) in a hydroxy(iso)flavone contribute to the antioxidant properties of the hydroxy(iso)flavone molecule and aid in the retention of the molecule within the matrix.

Phytochemicals are compounds naturally occurring in plants which often have antioxidant and/or anti-inflammatory properties, although the exemplary compounds may be extracted from plants or synthetically derived. Naturally occurring isoflavones, for example, are biologically active plant phenols or polyphenols found in a variety of plants, such as soybeans, fava beans, coffee, kudzu, psoralea, and *Flemingia vestita* (Fabaceae). When incorporated in the exemplary polymer composition, the hydroxyl(iso)flavone can exhibit strong antioxidant activity. The exemplary hydroxyisoflavone in the polymer composition is able to maintain this activity, which is useful for inactivating free radicals in the blood or body.

The modification agent can include at least one of a flavone, a substituted derivative of flavone, an isoflavone, and a substituted derivative of isoflavone. In one embodiment, the phytochemical includes at least one of a hydroxyflavone and a hydroxyisoflavone. The hydroxyflavone or hydroxyisoflavone can be a mono-, di-, tri, or tetra-hydroxyisoflavone (i.e., 1, 2, 3, or 4 of the hydrogens of the flavones or isoflavone molecule are substituted with a hydroxyl group), e.g., a tri-hydroxyisoflavone. The hydroxyflavone or hydroxyisoflavone may further include one or more additional substituents, such as an alkoxy and/or glucose moiety. In one embodiment, the phytochemical includes a hydroxyisoflavone, such as a mono-, di- or trihydroxy isoflavone.

To illustrate possible substituents, the isoflavone structure is shown below.

Isoflavone (3-phenyl, 1,4-benzopyrone)

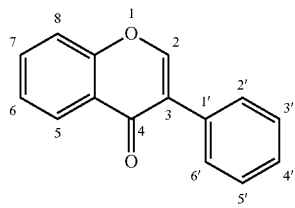 [SMILES: O=c1c(-c2ccccc2)coc2ccccc12]

In one embodiment, the hydroxyisoflavone is a substituted derivative of isoflavone, being related to the isoflavone molecule by the replacement of one, two, three, or four hydrogen atoms with hydroxyl groups. In some embodiments, the isoflavone structure may be additionally substituted with one or more alkoxy group, e.g., methoxy or ethoxy groups.

For example, the hydroxyisoflavone can have the structure of Structure I:

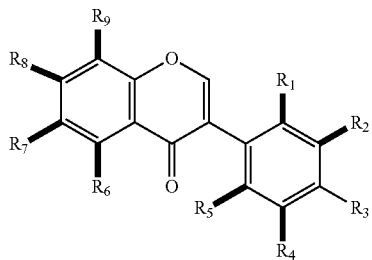

where $R_1$, $R_2$, $R_3$, $R_4$, $R_5$, $R_6$, $R_7$, $R_8$ and $R_9$ are independently selected from H, OH alkoxy, and glycosyl, and at least one of $R_1$, $R_2$, $R_3$, $R_4$, $R_5$, $R_6$, $R_7$, $R_8$ and $R_9$ includes an OH.

For example, the hydroxyisoflavone can have the structure of Structure II:

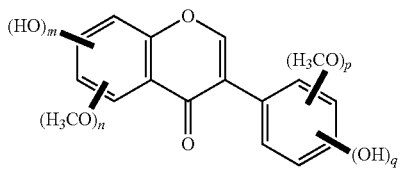

where m, n and p can independently be 0, 1, or 2 and q is 1 or 2. In some embodiments, the structure may further be substituted with one or more glucoside groups. In one embodiment, m is 2. In another embodiment, n is 0. In another embodiment, p is 0. In another embodiment, q is 1. The exemplary hydroxyisoflavone is a non-glycosylated isoflavone.

In one embodiment, there is a first hydroxyl at the 4' position of the isoflavone. In another embodiment, there is also at least a second hydroxyl at one or both of the 5 and 7 positions.

Exemplary hydroxyisoflavones are selected from:
genistein (5,7-dihydroxy-3-(4-hydroxyphenyl)chromen-4-one, also known as 4',5,7-trihydroxyisoflavone) with the following structure:

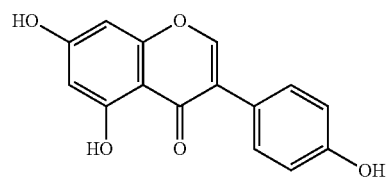 [SMILES: O=c1c(-c2ccc(O)cc2)coc2cc(O)cc(O)c12]

daidzein (7-hydroxy-3-(4-hydroxyphenyl) chromen-4-one (IUPAC), or 4',7-dihydroxyisoflavone), with the following structure:

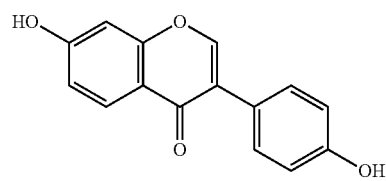 [SMILES: O=c1c(-c2ccc(O)cc2)coc2cc(O)ccc12]

glycitein (7-hydroxy-3-(4-hydroxyphenyl)-6-methoxy-4-chromenone (IUPAC), or 4',7-dihydroxy-6-methoxy-isoflavone),
prunetin (5-hydroxy-3-(4-hydroxyphenyl)-7-methoxy-chromen-4-one, or 4',5-dihydroxy-7-methoxyisoflavone),
biochanin A (5,7-dihydroxy-3-(4-methoxyphenyl)chromen-4-one, or 5,7-dihydroxy-4'-methoxyisoflavone),
orobol (3-(3,4-dihydroxyphenyl)-5,7-dihydroxychromen-4-one, or 3',4',5,7-tetrahydroxyisoflavone),
santal (7-methoxy-5,3',4'-trihydroxyisoflavone),
pratensein (5,7-dihydroxy-3-(3-hydroxy-4-methoxyphenyl) chromen-4-one, or 4'-methoxy-3',5,7-trihydroxyisoflavone),
formononetin (7-hydroxy-3-(4-methoxyphenyl)chromen-4-one, or 7-hydroxy-4'-methoxyisoflavone),
and glucosides, β-glycosides, and a koxy substituted derivatives thereof and combinations thereof.

The isoflavone of the polymer composition may include at least one of the group consisting of genistein and daidzein. The isoflavone in the polymer composition may comprise a mixture of two or more isoflavones.

The hydroxyisoflavone may comprise an isolated naturally occurring isoflavone. It can be extracted from a number of plants including soybeans, fava beans, kudzu, coffee, and combinations thereof. For example, the hydroxyisoflavone may be a soy-derived hydroxyisoflavone.

In other embodiments, the hydroxyisoflavone can be artificially synthesized. Methods for synthesis of genistein are described, for example, in Yohei Katsuyama et al., "One-pot synthesis of genistein from tyrosine by coincubation of genetically engineered *Escherichia coli* and *Saccharomyces cerevisiae* cells," Applied Microbiology and Biotechnology Volume 73, Number 5, 1143-1149 (2007).

Genistein is of particular interest as a hydroxyisoflavone because of the opportunity for delivery of health-promoting compounds. It has a molecular weight of 270 g/mol and melts at 306° C. Significant correlations have been found between an isoflavone-rich soy-based diet and reduced incidence of breast cancer or mortality from prostate cancer in humans. Genistein also inhibits DNA topoisomerase and tyrosine protein kinase, as well as possessing antioxidant and cell cycle inhibitor activity. Kinase inhibition is generally regarded as being specific for tyrosine kinases, such as epidermal growth factor (EGF) receptor, although at higher concentrations genistein also inhibits protein histidine kinase. These compounds are also produced by activated cells of the immune system and may be the cause of tissue damage. Additionally, peroxidation processes have been implicated in atherosclerosis etiology, especially the oxidative modification of LDL. Genistein has also been shown to reduce $H_2O_2$ production in HL-60 cancer cells and human polymorphonuclear cells in a dose dependent manner. It also has been shown to suppress superoxide anion formation and exogenous production of $H_2O_2$. It also has the ability to prevent LDL oxidation in presence of copper ions, superoxide, or nitric oxide radicals. Genistein also has been shown to protect the human endothelial cells from damage cause by oxidized LDL. In addition to its antioxidants properties, genistein has also been shown to be a good immunosuppressive agent, showing suppression of lymphocyte activation.

Most of the beneficial health effects of flavonoids are attributed to their antioxidant and chelating abilities, by virtue of their capacity to inhibit LDL oxidation, transfer electrons free radicals, chelate metal catalysts, activate antioxidant enzymes, reduce alpha-tocopherol radicals, and inhibit oxidases. By comparing biochemical a actions of genistein with those of related (iso)flavonoids in various experimental models, it may be evaluated which part of genistein's structure is responsible for its respective property and identify alternative compounds for forming the exemplary polymer. Estrogenic effects of genistein using MCF-7 breast cancer cell line cultured in vitro have yielded highly promising results. It has also been suggested that the 4'-hydroxy group seems to be the most important structure requirement for estrogenic activity of genistein because when the substituent is methylated or its position is altered by shifting the phenolic C ring from 3- to 2-position binding on the pyran ring, ER binding and estrogenicity are reduced 10-fold. As regards the antiproliferative effects of genistein and related compounds, the 5-hydroxy group and 4-ketonic oxygen seem to be necessary for (iso)flavonoids to be growth inhibitory. The PTK inhibitory activity of genistein decreases drastically either by the removal of a hydroxyl group from the 5 position or by the addition of a methoxy group to 4' position. It is thought that addition of a methoxy group at the 7 position, such as an O-glucose, completely eliminates the activity and that at 7 and 4' positions is necessary for full expression of the activity. To summarize, genistein has two principal biochemical properties related to its chemical structure. The first one is its estrogenicity—common to other isoflavonoids having a free hydroxyl group at position 4' and 7. The second property is the ability of genistein to inhibit some of cellular enzymes.

The hydroxy(iso)flavone may constitute from 1-65% by weight of the solid polymer composition, e.g., at least 1 wt. % or at least 10 wt. % or at least 20 wt. % of the polymer composition. In one embodiment, hydroxy(iso)flavone is present at up to 50 or 60 wt. % of the polymer composition, and in another embodiment, it is present up to 35 wt. % or 40 wt %. In some embodiments, the hydroxy(iso)flavone is present at from 20-35% wt. % of the polymer composition. The hydroxy(iso)flavone may constitute up to 60% by weight of the polymer composition when the matrix material includes a polyethersulfone. Expressed as a ratio of hydroxy (iso)flavone: matrix material by weight, the ratio may be from 1:99 to 60:40, and in one embodiment, the ratio is from 10:90 to 40:60. In particular, the hydroxy(iso)flavone is a hydroxy-isoflavone in these percentages/ratios.

The hydroxy(iso)flavone may be miscible with the component(s) of the matrix material and/or dispersed in the matrix material. The resulting biocompatible polymer may thus be a solid polymer composition in which the isoflavone is dispersed fairly homogeneously. In other embodiments, the isoflavone may be concentrated at surfaces of the biocompatible polymer.

The exemplary genistein-modified polymers have been found to reduce serum levels of certain cytokines as well as promoting a reduction in reactive oxygen species (ROS), which are known to play an important role in mutagenesis, carcinogenesis and particularly in tumor promotion. Genistein can inhibit both the priming events necessary for high level ROS production.

The anti-oxidant properties of genistein can be understood by considering the mechanism of formation of oxygen radicals. Upon activation of the cells, the membrane-bound nicotinamide adenine dinucleotide phosphate (NADPH) and cytosolic components of the enzyme assemble in the membrane and form the active enzyme. NADPH oxidase catalyzes the reduction of $O_2$ to superoxide anion ($O_2^{\cdot-}$), which then rapidly dismutates to hydrogen peroxide ($H_2O_2$). This chain of events is referred to as an electron transport chain. Subsequently, $H_2O_2$ may be converted by the enzyme myeloperoxidase into highly reactive compounds such as hypochlorous acid (HOCl). Therefore, for a neutrophil to undergo oxidative burst, a functionally intact NADPH oxidase may be crucial. In this case, genistein successfully inhibited the expression of NADPH, which is the first step of the electron transport chain to form superoxide anion and subsequent dismutation to $H_2O_2$.

While the exemplary actives in the biocompatible polymer disclosed herein are isoflavones, other antioxidants/phytochemicals which are capable of being retained within a polymer matrix, e.g., by hydrogen bonding, and yet provide antioxidant or other beneficial properties to the polymer composition when brought into contact with a free-radical containing liquid, such as blood or other body fluid, are also contemplated. In some embodiments, for example, the polymer composition may further include a xanthone, as disclosed for example, in copending application PCT/US09/66166. In one embodiment, the xanthone is a hydroxylated xanthone which includes at least one hydroxyl group or hydroxyl-containing group, and can be glycosylated or non-glycosylated. Mangiferin is an exemplary glycosylated xanthone represented by the following structure:

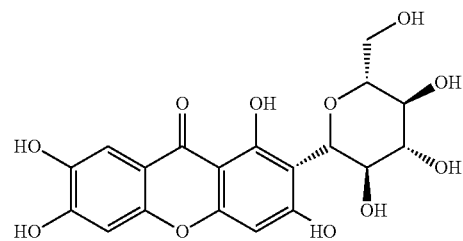

Mangiferin is a naturally occurring glycosylated xanthone which can be obtained from barks, leaves and fruits of *Mangifera indica* (Mango Tree). However, it is also anticipated that a synthetic form of mangiferin may be used. It has a molecular weight of 422.35 grams/mole, and melts at 271° C. When present in the polymer composition, it is able to provide the composition with some or all of anti-oxidant, anti-tumor, anti-viral, anti-bacterial, anti-fungal, anti-platelet, anti-thrombotic, anti-inflammatory, immunomodulatory and anti-diabetic properties.

Examples of other non-glycosylated xanthones which may be used herein include 1,3,6,7-tetrahydroxyxanthone (norathyriol), 1,3-dihydroxyxanthone, 1,6-dihydroxyxanthone, 1,3,7-trihydroxyxanthone, 1,3,5,6-tetrahydroxyxanthone, 2,3,6,7-tetrahydroxyxanthone, 3,4,5,6-tetrahydroxyxanthone, and combinations thereof.

The Matrix Material

The matrix material may be selected from the group consisting of polysulfones, polyamides, polyvinylpyrrolidones, polycarbonates, polysulfones, polyacrylonitriles, and multiples and combinations thereof. The polysulfone may be a polyethersulfone. As examples, the matrix material may include one or more of poly(amide) (PA), poly(amide):poly(vinyl pyrrolidone) (PA:PVP), poly(ethersulfone) (PES), and poly(ethersulfone):poly(vinyl pyrrolidone) (PES:PVP), or consist essentially of such materials (be at least 80 wt % or at least 90 wt % of one or more of these materials). The matrix material can be derived from one or more homopolymers or from monomers of such polymers which react to form a polymer or copolymer. In some embodiments, the polymer matrix may additionally comprise one or more of polycarbonates, polyacrylonitriles, and combinations thereof.

In one embodiment, the matrix material may comprise a blend of polymer forming materials. The blend may include a polyvinylpyrrolidone and a thermoplastic polymer. The thermoplastic polymer may include at least one of a polyamide and a polyethersulfone. In an exemplary embodiment, the matrix material is formed from a blend of homopolymers, such as a blend of a polyamide and/or polyethersulfone and polyvinylpyrrolidone. In one specific embodiment, the matrix material is predominantly formed from homopolymers selected from this group (i.e., at least 50%). The polyamide and/or polyethersulfone may constitute from 5-100% by weight of the matrix material, such as at least 40% or 50% by weight of the matrix material, and in one embodiment, up to 95% by weight of the matrix material. Polyvinylpyrrolidone may supply the balance, by weight. The finished polymer may have an analogous ratio of polymers as its matrix component.

"Polysulfones," as used herein, refers to a family of thermoplastic polymers which contain the subunit -aryl-$SO_2$-aryl-, more specifically -aryl-$SO_2$-aryl-O—, and includes a polymer of 4-[2-(4-hydroxyphenyl)propan2-yl]phenol and 4-(4-hydroxyphenyl)sulfonylphenol, commonly known as polysulfone, and a polymer of benzene-1,4-diol and 4-(4-hydroxyphenyl)sulfonylphenol commonly known as polyethersulfone. Polyethersulfone (PES) is also known as polyarylethersulfone (PAES) and/or polyphenylsulfone (PPSU). Another suitable polysulfone is a copolymer of 4-(4-hydroxyphenyl)phenol and 4-(4-hydroxyphenyl)sulfonylphenol, also known as polyphenylsulfone. Other exemplary polysulfones are described in U.S. Pat. No. 5,911,880, the disclosure of which is incorporated herein by reference in its entirety. In one embodiment, the matrix material includes homopolymers of two or more of these polymers, e.g., a combination of a hydrophobic homopolymer(s) and a hydrophilic homopolymer(s).

In an exemplary embodiment, the matrix material is formed from a blend comprising a mixture of polyvinylpyrrolidone (PVP) and one or both of polyamide (PA) and polyethersulfone (PES) and which may be substantially free of other polymers (i.e., less than 10 wt % of other polymers and in one embodiment, less than 5 wt % of other polymers). The polyethersulfone and/or polyamide may constitute from 5-95% by weight of the PES/PVP, PA/PVP or PES/PA/PVP blend, e.g., at least 40% by weight, or at least 50% by weight of the blend. In an embodiment, a PA/PES/PVP blend may be used to refine the final properties of the membranes and can be included as part of the optimization process.

In one aspect, a biocompatible polymer composition may consist essentially of a polyamide and/or polyethersulfone, polyvinylpyrrolidone and at least one hydroxyisoflavone at a concentration of, for example, at least 1 wt %, or at least 5 wt %, with other components accounting for no more than 10 wt % of the polymer composition and in one embodiment, no more than 5% wt % of the polymer composition. The at least one of a polyamide and a polyethersulfone may be present in the blend at least 5 wt %, e.g. at least 40 wt. %, at least 50 wt. %, up to 95 wt %.

The polymer composition and hence a product formed from it which is to be inserted into the human body or used in the filtration of blood, such as a membrane, is a solid at ambient temperatures and above. In the exemplary embodiment, the polymer composition is a solid at a temperature of at least 30° C. By "solid," it is meant that the product retains a shape sufficient to perform the intended purpose at the desired temperature. In the case of a membrane, the polymer composition is a solid at the temperature of the blood passing through the filter, which may be up to about 38° C. (the temperature of human blood in the body). The polymer composition may, of course be solid at higher temperatures. In the solid polymer composition, the homopolymers of the blend may be in the form of a block copolymer or are held together by weaker bonds, such as hydrogen bonds, or a combination thereof.

Filter Unit

FIG. 1 is a schematic diagram of a simplified hemodialysis circuit 10 including a dialyzer filter unit 20 including a container or housing 21 containing an semi-permeable membrane 22 formed at least partially from the exemplary biocompatible polymer composition. The membrane 22 may be formed substantially or exclusively from the biocompatible polymer composition. In other embodiments, the biocompatible polymer composition provides a surface layer or layers on a supporting structure, such as a hollow fiber.

Blood from a patient 24 is removed through a venous blood line 26 with a blood pump 28 supporting circulating blood and optionally through a heparin pump 30 towards the dialyzer filter unit 20. During dialysis, blood flows through the semi-permeable membrane 22 in one direction, with a dialysis solution flowing in the opposite direction. The dialysis solution is injected into the filter unit 20 at a fresh dialysate port 32. Due to the difference in osmolarity between the two liquids, water traverses the membrane 22 in order to dilute the dialysis liquid, carrying along the impurities from the blood. The impurities are ejected through a used dialysate port 34. The dialysis fluid is used at body temperature, and may include a solution of glucose, amino acids and mineral ions. The cleansed blood is then returned to the patient 24 through a clean return blood line 36. Some or all of the components 26, 28, 30, 36 which come into contact with the blood may additionally or alternatively be formed from the exemplary biocompatible polymer composition and/or coated with a surface layer formed from the polymer composition.

The semi-permeable membrane 22 is at least partially permeable to water and may allow certain molecules or ions to pass through it by diffusion and occasionally specialized "facilitated diffusion." The rate of passage may be dependent on pressure, concentration, and temperature of the molecules or solutes on either side, as well as the permeability of the membrane to each solute. Depending on the membrane and the solute, permeability may depend on solute size, solubility, properties and/or chemistry. The exemplary semi-permeable membrane 22 reduces ROS and/or cytokine concentration in the patient's blood, as compared with a conventional membrane, and optionally provides additional benefits, such as anti-oxidant, anti-inflammation, anti-bacterial, anti-viral, anti-diabetic, and/or non-thrombogenic properties.

Figure 2:
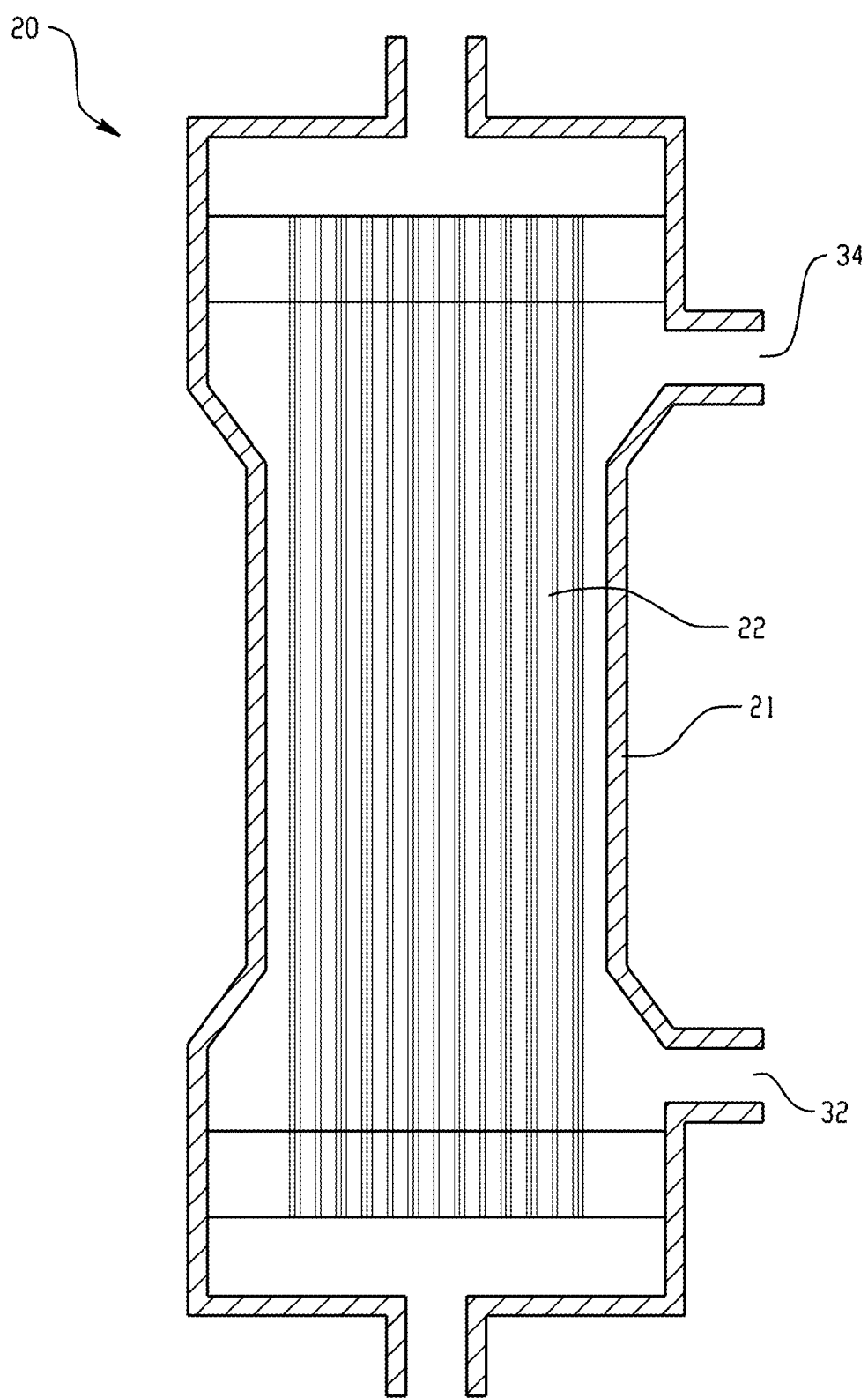
FIG. 2 is a schematic cross-sectional view of the dialyzer filter of FIG. 1.

FIG. 2 shows a cross-sectional view of the filter unit 20 containing the membrane 22. The semi-permeable membrane 22 may be in the form of a thin film or an arrangement of fibers, such as a bundle of hollow fibers, as shown. In other embodiments, the membrane is in the form of a porous sponge or other porous structure which allows blood to pass therethrough. A typical number of hollow fibers within a dialyzer filter unit may range from 7,000-14,000. The dialyzer can be designed so that the patient's blood flows inside the hollow fibers, which can have an inner diameter of about 180-200 µm. The dialysate flows around the outside of the membranes. The wall thickness of the hollow fibers depends on the membrane polymer and can vary from 10-50 µm.

Figure 3:
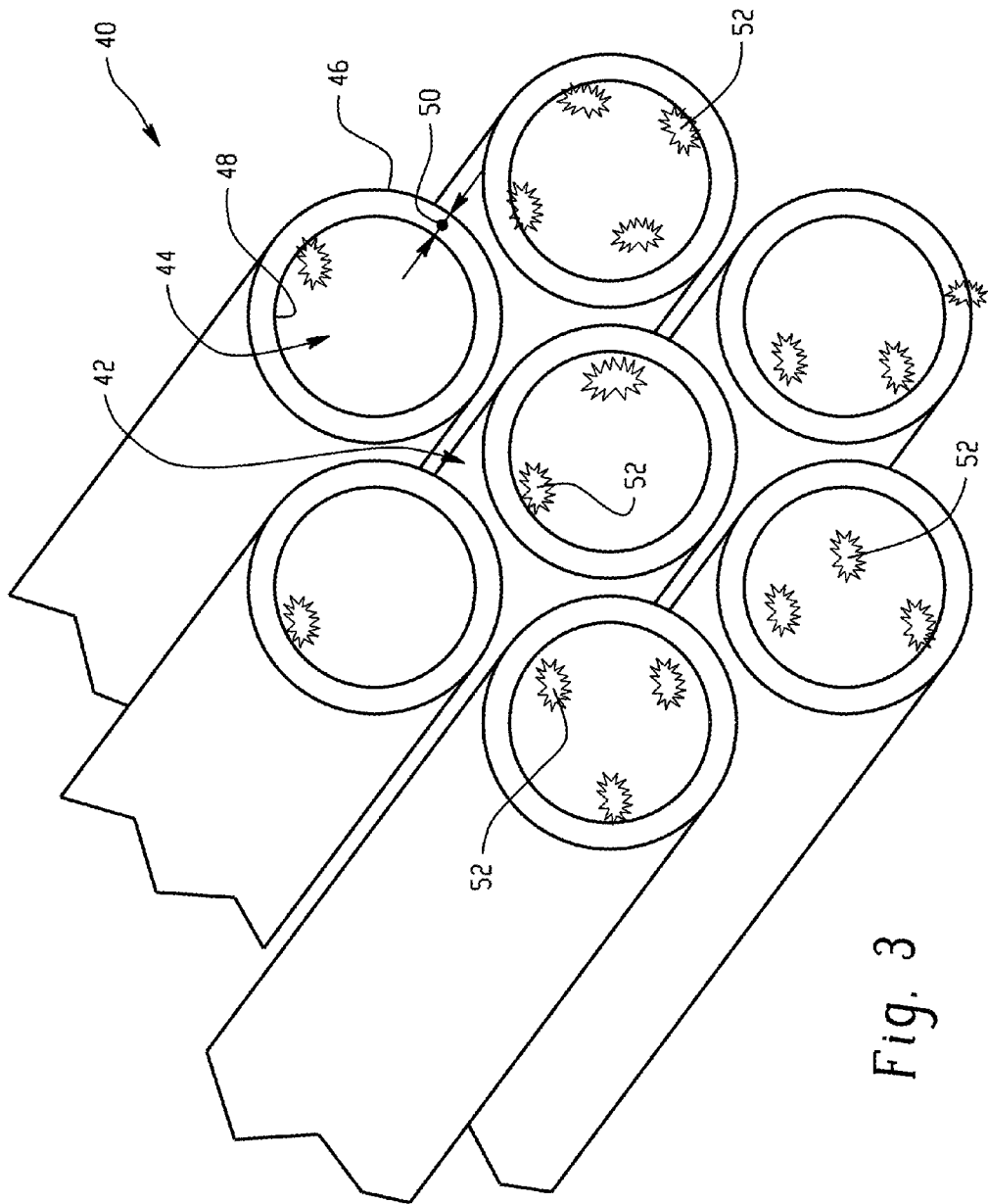
FIG. 3 is a schematic perspective view, in partial cross-section of an array of hollow fibers within an exemplary semi-permeable membrane formed from the biocompatible polymer composition.

FIG. 3 shows a perspective view in partial cross-section of a portion of an exemplary membrane 22 comprising an array of hollow fibers 40. The fibers may be arranged generally in parallel, with spaces 42 between the fibers. Hollow fiber 40 may have a continuous hollow cavity 44, which extends from one end to the other end of the fiber, an outer wall surface 46 which forms an outer side of the fiber, and an inner wall surface 48 which defines the limits of the continuous hollow cavity 44. A wall thickness 50, measured between the outer wall surface 46 and the inner wall surface 48 of the hollow fiber 40, may be less than 100 µm, e.g., from 5-50 µm, such as from 5-35 µm. The cross-sectional diameter of the fibers may be less than 200 µm, e.g., from 10-100 µm, such as from 20-70 µm. In some cases, the genistein in the biopolymer may be at least partially at the surfaces 46, 48, e.g., in the form of crystals 52.

The exemplary dialyzer filter unit 20 can be formed by forming a semi-membrane 22 from the polymer composition, and inserting the semi-membrane 22 into the dialyzer filter unit housing 21.

The filter unit 20 can be used for filtering any blood or any other free-radical containing fluid. In one embodiment, a method of removing free radicals from a fluid includes filtering a fluid with the semi-permeable membrane 22 described above, whereby free radicals in the fluid pass through by the semi-permeable membrane 22 and are removed from the fluid.

While the biocompatible polymer composition has been described in terms of a hemodialysis filter which can be used for hemodialysis and/or hemofiltration, it is also contemplated that it may be used in the forming of other medical devices, including medical tubing, such as a vascular implant, a vascular graft, stent, stent graft, or catheter for insertion into the vascular system of a living being. The medical device may include, in at least a surface layer thereof, at least one anti-oxidant, such as a hydroxy(iso)flavone, as described above, at a concentration of at least 0.1 wt %, and/or which may include a polymer matrix as described above.

Forming the Biocompatible Polymer Composition and Membrane

Porous membranes can be prepared from the exemplary matrix material and modification agent by several methods such as sintering, stretching, track etching and phase separation processes. The membranes can be formed using controlled phase separation of a polymer solution into a polymer rich and polymer poor phase. Phase separation can be achieved, for example, in the following ways:

1. Thermally induced phase separation (TIPS): A solvent which acts as good solvent at high temperature loses its quality with decreasing temperature leading to phase separation. The solvent is removed by extraction, evaporation, or freeze drying.

2. Air-casting of a polymer solution: A polymer is dissolved in a mixture volatile and less volatile non-solvent. After casting the film the more volatile solvent is allowed to evaporate. This increases the less volatile non-solvent concentration leading to reduction in solubility of polymer and thus phase separation takes place 3. Precipitation from a vapor phase: A polymer solution is cast in an atmosphere saturated with non-solvent vapor. Phase separation is induced by vapor diffusion into the polymer solution leading to phase separation.

4. Non-solvent induced coagulation: Here a polymer solution is cast or spun in form of a film or fiber and subsequently immersed into a non-solvent bath. Solvent/non-solvent exchange occurs across the interface, thus making the polymer solution thermodynamically unstable leading to the phase separation. This process can be carried out under ambient conditions.

Solutions of neat (or undiluted) PA, PVP, hydroxy(iso)flavone and their blends can be prepared in a suitable solvent in which all components are soluble. In an exemplary embodiment, the method of forming the biocompatible polymer composition includes combining the matrix material and at least one isoflavone in the presence of a solvent, thereby forming a matrix material/isoflavone/solvent blend. Exemplary solvents include polar solvents. The solvent can be at least one of dimethylsulfoxide (DMSO), dimethylacetamide (DMA), and dimethyl formamide (DMF). DMSO is used in the Examples below due to its capability of dissolving PA, PES and PVP and the phytochemicals used and is accepted as being pharmacologically benign. The matrix material/(iso)flavone/solvent blend is a liquid. The matrix material and (iso)flavone may together constitute from 1-25% by weight of the matrix material/(iso)flavone/solvent blend, e.g., at least 5% by weight, or at least 10% by weight of the blend. The PA: PVP and PES: PVP ratios in the blends may be from 1:99 to 99:1, e.g., from 10:90 to 90:10, and in one embodiment from 40:60 to 70:30, e.g., greater than 50:50. The (iso)flavone: matrix material ratio in the liquid blend may be from 1:99 to 99:1, e.g., less than 50:50. It is to be appreciated that, particularly at high isoflavone concentrations, a portion of the isoflavone does not end up in the membrane, resulting in lower than expected concentrations in the final solid polymer composition/membrane. The solvent may be present in a reaction vessel at about 70-95 wt %, e.g., 90 wt %, i.e., at a polymer concentration of 10 wt %.

The liquid mixture of polymer forming components (e.g., hydroxyisoflavone, PA, PES, and/or PVP) and solvent can be stirred or homogenized in a reaction vessel at a suitable temperature (e.g., ambient room temperature) for sufficient time for the components to mix thoroughly (e.g., for at least 48 hours) to form a matrix material/hydroxyisoflavone/solvent liquid blend. Ambient temperature can be considered to be from about 18° C. to about 28° C. Thereafter, the liquid mixture can be formed into a membrane, e.g., by solvent casting under vacuum at 150° C. for 24 hours or other methods for forming a membrane/solid polymer composition which result in removal of solvent or reduction in solvent concentration.

In another embodiment, a melt blending process can be used to form the biocompatible polymer composition. A suitable composition ratio of matrix material (e.g., PA/PES and/or PVP) is combined in a reaction vessel and heated to above the glass transition temperature(s) ($T_g$), which ranges from 140° to 160° C., but below their decomposition temperatures, for up to 20 minutes. For example, the mixture of homopolymers may be heated up to about 250° C. When the mixture is viscous or exhibits a high resistance to flow, an amount of isoflavone, e.g., genistein, is added and mixed for up to 5 minutes. In some embodiments, a small amount of solvent, such as dimethylsulfoxide, may be added to the mixture to provide better homogenization. The solvent may be later removed. It may be appreciated that the melt blending process can alternatively be used to form a PES/PVP/genistein/dimethylsulfoxide liquid blend.

The polyamide, polyethersulfone, and/or polyvinylpyrrolidone used for forming biocompatible polymer compositions may be homopolymers. Prior to mixing, the homopolymers may each have a weight average molecular weight ($M_w$) from 1,000 to 3 million grams/mole, e.g., at least 10,000 grams/mole, such as at least 20,000 grams/mole or at least 30,000 grams/mole. In one embodiment, $M_w$ for each homopolymer is less than 200,000 grams/mole, e.g. less than 100,000 grams/mole.

The polyamide and polyethersulfone used for forming the blends may be amorphous or semi-crystalline polymers. In amorphous polymers, the membrane formation is not complicated by the matrix crystallization. Typically, aliphatic polymers may tend to be crystalline as the monomer units can pack inside a crystalline lattice. However, the addition of aromatic units may disrupt the crystalline packing. At high aromatic contents the system tends to be amorphous. Aliphatic/aromatic refers to the chemical composition of the monomers that constitute the polymer. Amorphous refers to the physical property wherein the polymer is not able to crystallize. Exemplary polyamides include amorphous polyamides having a glass transition temperature $T_g$ of at least about 140° C. Exemplary polyamides include nylon, such as, nylon-6, nylon-6,3, nylon-6,6, nylon-6/3T, and combinations, thereof. Exemplary polyethersulfones include amorphous polyethersulfones having a glass transition temperature $T_g$ of at least about 230° C. Other forms, such as aliphatic and aromatic polyamides and polyethersulfones, may be used for example, where strong acids such as sulfuric, hydrochloric, methane sulfonic acid and formic acid, are used to form the initial solution. Exemplary polyethersulfones include those sold by BASF under the trade name of ULTRASON® E, such as ULTRASON® E 6020P.

In the PA/PVP and PES/PVP blends, the polyvinylpyrrolidone homopolymer imparts hydrophilicity and the amorphous polyamide and polyethersulfone homopolymers impart hydrophobicity. The amorphous polyamide and polyethersulfone homopolymers additionally exhibit viscoelastic properties to form good films and fibers. The viscoelasticity allows the composition to undergo deformation when a stress is applied.

The polymer composition can be isolated by immersion of the matrix material/hydroxyisoflavone/solvent mixture into a non-solvent, such as water. The non-solvent displaces the solvent in the mixture inducing phase separations the mixture. One or more of the phases may be selected, depending on the desired polymer composition. In other embodiments, the solvent may be removed through evaporation.

Fibers 40 for the semi-permeable membrane 22 may be fabricated from the polymer composition (which may be in the form of a solvent-containing liquid blend or solvent-free) according to a variety of methods known in the art including electrospinning, gas jet (NGJ), wet spinning, dry spinning, melt spinning, and gel spinning. Some of these methods start with a solution of a fiber-forming polymer dispersed in a suitable solvent. In the electrospinning method, for example, an electrical potential is applied between a droplet of the solution and a collector positioned below it. The droplet extends rapidly under the applied potential. The solvent evaporates from the solution, forming fibers before they reach the collector. Electrospinning tends to produce very thin (i.e. fine denier) fibers. Typically, electrospun fibers have very small diameters, usually on the order of about 3 nanometers to about 3000 nanometers.

A suitable method for producing hollow fibers is known as the fibers by gas jet (NGJ) method. In this method, a device having an inner tube and a coaxial outer tube with a sidearm is provided. The inner tube is recessed from the edge of the outer tube, thus creating a thin film-forming region. Polymer melt is fed in through the sidearm and fills the empty space between the inner tube and the outer tube. The polymer melt is prepared by the melt blend process as described above. The polymer melt continues to flow toward the effluent end of the inner tube until it contacts the effluent gas jet at the edge of the inner tube where it opens into the outer tube. The gas jet impinging on the melt creates a thin film of polymer melt in the region between the edges of the inner and outer tubes, which travels to the effluent end of the outer tube where it is ejected forming a turbulent cloud of hollow fibers. In the present embodiment, the polymer melt comprises the matrix material and a isoflavone.

In another exemplary embodiment, the fibers 40 are formed by solution spinning. These fibers can be produced from a solution of the two homopolymers, a hydroxy(iso)flavone, and a solvent, such as dimethylsulfoxide, by spinning the solution through an appropriately constructed shaping annular die of a hollow-needle nozzle into a precipitation liquid. An example of a precipitation liquid which may be used is water. The production conditions can be tailored in such a way that an external skin or an internal skin or both are formed. The wall thickness of hollow fibers 40 of this type is usually in the range from about 5 to 500 µm.

To form the membrane, the fibers 40 can be held together as a bundle, e.g., by sealing the edges of the fiber bundle using an epoxy.

Other methods for forming fibers 40 and semi-permeable membranes 22, which may be used herein, are disclosed, for example, in U.S. Pat. Nos. 4,935,141, 5,505,851, 5,152,894, 6,382,526 and 6,520,425, and U.S. Pub. No. 2007/0207179, the disclosures of which are incorporated herein by reference.

The exemplary membranes 22 formed from the polymer composition using genistein as the active are able to reduce reactive oxygen levels and levels of some cytokines. Cytokines are a family of proteins that are involved in numerous immunological functions including the production and control of other cytokines. They play an important role in the regulation of hematopoiesis, mediating the differentiation and proliferation of diverse type of cells. For example, it has been identified that endotoxins (such as bacterial components) from dialysate induce secretion of IL-1β from neutrophils, which causes fever and low blood pressure during hemodialysis. IL-1β and TNF-α are known for their autocrine (i.e., induce/regulate its own secretion) and paracrine signaling (induce/regulate other cytokine secretion) functions. Clinically, it has been demonstrated that serum concentrations of IL-1β and TNF-α raise several folds during hemodialysis in a manner dependent on the choice of the membrane. Although a polymeric membrane surface could induce cytokine secretion due to direct contact of PBMC with membrane and endotoxin from dialysate, complement-mediated cytokine secretion has been generally accepted as the common mechanism by which hemodialysis membranes induce inflammation. In the case of hemodialysis, the alternate pathway of complement activation leads to the formation of complement fragments such as C3b, which coats the membrane surface by adsorbing to the membrane surface. C3b molecules together with other soluble complement fragments such as C3a and C5a subsequently stimulate the PBMC triggering the enhanced secretion of pro-inflammatory cytokines.

Without intending to limit the scope of the exemplary embodiment, the following examples demonstrate properties of the composition.

EXAMPLES

Genistein modified poly(amide):poly(vinyl pyrrolidone) (PA:PVP/G) hemodialysis membranes have been fabricated by coagulation via solvent (dimethyl sulfoxide, DMSO)/non-solvent (water) exchange. The anti-oxidant and anti-inflammatory properties of the unmodified PA:PVP membranes were evaluated in vitro using human blood. It was found that these unmodified PA:PVP membranes were non-cytotoxic to peripheral blood mononuclear cells (PBMC), but raised intracellular reactive oxygen species (ROS) levels. Pure genistein (in DMSO solution) was not only non-toxic to PBMC, but also suppressed the ROS levels in a manner dependent on genistein dosage. A similar dose-dependent suppression of ROS was found in genistein modified PA (i.e., PA/G) membranes. However, the PVP addition had little or no effect in the suppression of ROS levels for the ternary PA:PVP/G system; the membrane ROS suppression was largely controlled by the genistein dosage.

The levels of tumor necrosis factor-α (TNF-α), interleukin-1β (IL-1β) and interleukin (IL-6) in whole blood were measured by ex vivo stimulation with lipopolysaccharide (LPS). The unmodified PA:PVP membranes drastically increased the level of TNF-α; however the concentration of IL-1β and IL-6 remained almost the same. On the other hand, the PANG membranes reduced the concentration of IL-1β and TNF-α even at very low genistein loadings, but it required a higher genistein loading to realize a similar effect in the case of IL-6. Of particular importance is that the genistein modified blend membranes (PA:PVP/G) showed greater suppression of the concentrations of all three cytokines (TNF-α, IL-1β and IL-6) in comparison with those of the PANG membranes, signifying the role of PVP in the enhanced anti-inflammatory properties of these genistein modified membranes.

Materials

An amorphous polyamide nylon-6/3T (TROGAMID® T5000) ($M_n$=20,000 and $M_w$=63,000) (Degussa Corporation, N.J., USA) having a reported water absorption of 5.1 wt % was used as a polyamide (PA). The likely structure of PA is shown below:

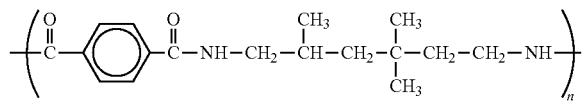

Polyvinylpyrrolidone (PVP) ($M_w$=40,000) was obtained from Sigma Aldrich (MO, USA). The structure of PVP is shown below:

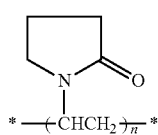

An amorphous polyethersulfone (ULTRASON® E 6020P) (Mw=46,000 and $T_g$=230° C.) (BASF Corporation) approved by the FDA and commonly employed in dialyzer membrane applications was used as the polyethersulfone. The structure of PES is shown below:

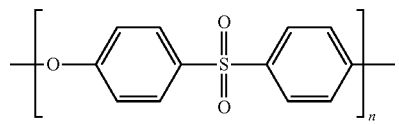

A reagent grade DMSO (dimethyl sulfoxide), obtained from Sigma-Aldrich (Mo, USA) was used as a common solvent without further purification.

Soybean-derived genistein (>98% purity) was obtained from MDidea Exporting Division (YinChuan, China).

Reverse osmosis grade water was utilized as a non-solvent for membrane formation. DMSO is highly soluble in water and traces can be removed from the membranes by repeated washing with water.

Dihydrorhodamine 123 (DHR) was obtained from Invitrogen (Carlsbad, Calif.).

Phorbol myristate acetate (PMA) was obtained from Sigma-Aldrich (Mo, USA).

Mangiferin ($M_w$=422.3 g/mol) was obtained from Sigma Aldrich, USA.

Fabrication of Genistein Modified PA:PVP Membranes

To inhibit moisture absorption, PA pellets were vacuum-dried at 80° C. for 24 h and subsequently dissolved in DMSO to form a feed solution. In the preparation of genistein modified membranes, various amounts of genistein were added to the feed solution. The solutions were homogenized for 48 hours by mechanical stirring and the entrapped air, if any, was removed under vacuum at room temperature. The homogeneous solutions were then cast in the form of a film of pre-determined thickness on a pre-cleaned glass plate, followed by immersion in a non-solvent bath (reverse osmosis grade water) maintained at 25° C. The coagulated membranes were peeled off from the glass plate, rinsed with excess water, and then vacuum dried at room temperature. For scanning electron microscope (SEM) observations, dried membrane samples were fractured in liquid nitrogen and then sputtered with silver using a sputter coater (Emitech, Model K575X). The sample surfaces were cleaned with compressed air before sputtering. The resulting samples were analyzed with field emission SEM (JEOL-Model JSM-7401F). SEM micrographs were taken at three different areas intended to be representative of the whole sample.

Reagents and Blood Samples

A stock solution of DHR (10 mg DHR in 2.0 ml DMSO) was stored in 50 µl aliquots at −70° C. For the assay, 20 µl of the DHR stock solution was dissolved in 980 µl PBS to give a final concentration of 100 µg/ml.

A PMA stock solution was prepared by dissolving 1 mg PMA in 1 ml DMSO. This solution was also stored in 50 µl aliquots at −70° C. Subsequently, 10 µl of PMA stock solution was diluted with 90 µl of PBS to give a final concentration of 5 µg/ml. The PMA stock solution was used to activate neutrophils (a type of white blood cell) to undergo oxidative burst (generation of ROS).

For the blood samples, 10 ml samples of venous blood were collected from a human donor in lithium heparin Vacutainer™ tubes (Becton Dickinson, Rutherford, N.J.) and used within 12 h of the collection.

Cytotoxicity Studies

Cell viability assays were conducted to determine the effect of unmodified membranes, pure genistein and genistein modified membranes on whole blood. A nucleic acid dye, 7-Amino-actinomycin D (7-AAD), (BD-Via-Probe™ from BD Bioscience, CA) was used as a viability probe, which is based on uptake of 7-AAD. 7-AAD is a nucleic acid dye, which is designed in such a way that it cannot enter live cells. Fresh blood mixed with the dye was used as a negative control, whereas blood incubated with the membrane and/or genistein served as the experimental samples.

To perform the assays, 100 µl of fresh blood was pipetted into separate polypropylene tubes and mixed with 2 ml of ammonium chloride lysis buffer solution (containing 8.26 g ammonium chloride, 1 g potassium bicarbonate, and 0.037 g ethylenediamine-tetraacetic acid dissolved in 1 liter deionized water). The tubes were allowed to stand at room temperature for 10 min during which most of the red blood cells were lysed. The tubes were centrifuged at room temperature for 5 min at 1,800 rpm. The supernatant was discarded and the cells were washed twice and centrifuged with 2 ml of phosphate buffer saline (PBS, Baxter, Ill., US. pH=7.4) solution. The supernatant was discarded again and 20 µl of 7-Amino-actinomycin D (7-AAD) dye (BD-Via-Probe™ from BD Bioscience, Calif.) was added to the cells and were stored under dark conditions for 10 min to permit cell uptake. The cells were resuspended with 500 µl of PBS and the cell suspension was analyzed using a flow cytometer (EPICS® XL-MCL™, Beckman Coulter, Calif., USA) equipped with System II™ software. In particular, the number of cells in each sample was adjusted to between 10,000 to 20,000 cells/ml using PBS. The fluorescence signal from the dead cells was measured on the FL3 red channel (650 nm) with the flow cytometer.

DHR Assay

In order to establish the reliability of the DHR (dihydrorhodamine) assay, 100 µl of whole blood samples were pipetted into three separate polypropylene tubes. These were labeled as stimulated, resting and reagent blank. Twenty-five micro liters of 5 µM PMA solution were added to the stimulated tubes and 25 µl PBS was added to the resting and reagent blank tubes. All tubes were incubated at 37° C. for 15 min. Then 25 µl working DHR solution were added to the stimulated and rested samples and 25 µl PBS was added to the reagent blank followed by 15 min incubation at 37° C. The tubes were centrifuged at 1,800 rpm for 5 min. The supernatant was discarded and the cells were washed and centrifuged twice. After the second centrifugation, the supernatant was discarded and replaced with 1 ml of immunoprep® (Beckman Coulter, Calif., USA) solution. Immunoprep® reagent is a rapid whole blood lysing solution consisting of three ready-to-use reagents, which lyses the red blood cells, buffers the solution to stop the lysing process and fixes the cells, respectively. The solutions were filtered through a 50 µm filter to remove the cellular aggregates. The samples were analyzed using the flow cytometer described above. A quality control run was executed daily according to the manufacturer's instructions to ensure proper calibration of the instrument. Before acquiring data, the instrument was set up using a reagent blank sample. The forward and side light scatter profiles were adjusted to ensure that the neutrophil population was well resolved. Fluorescence was measured on the FL1 green channel (wavelength 530 nm). Data were then collected from the reagent blanks and all resting and stimulated tubes. A total of 10,000 events were collected for each sample. During analysis, the plot of forward scattering vs. side scattering was displayed and the neutrophil population was identified by its typical location, and selected by gating. Subsequently, a histogram of rhodamine fluorescence (FL1) was obtained for the gated region and the mean channel fluorescence was recorded. Each experiment was repeated three times.

DHR Assay with Genistein and Unmodified and Genistein-Modified Membranes

In order to determine the effect of membranes and/or genistein on oxygen radical generation, the standard dihydrorhodamine (DHR) assay was modified as follows. The assay consisted of one positive control tube, several sample tubes and one negative control tube. The positive control tube contained 100 µl blood, 25 µl DHR, and 25 µl PMA; the total contents were made up to a total volume of 1 ml with PBS. The effect of oxygen radical generation is tested as follows, using the sample tube containing 100 µl blood, 25 µl DHR, 25 µl PMA and the appropriate sample (for example, unmodified membranes or pure genistein or genistein modified membranes). The membranes were cast and dried under sterile conditions inside a biosafety laminar flow hood. For the assay, two small circular samples ($2 \times 0.4$ cm$^2$) were punched out from the cast films and placed inside the test tubes. After adding the membrane, the entire contents were incubated at 37° C. for 3 h (to simulate hemodialysis conditions) while being subjected to continuous shaking. After 3 h of incubation, the membrane samples were removed from the blood and agitated with 1 ml of PBS in order to dislodge the cells that were attached to the membrane. In the case of pure genistein (i.e., no membrane), the samples were prepared by dissolving genistein in DMSO over a wide range of concentration (25-500 µg/ml). The negative control tube contained 100 µl blood, 25 µl DHR, and the sample. The rest of the assay was similar to the standard DHR assay protocol including lysis of red blood cells, fixing of cells with immunoprep® solution and followed by flow cytometric analysis.

In order to normalize the data obtained from different set of experiments, the following formula was employed to express ROS level in percentage, $$\% \ ROS \ \text{level} = 100 - \left(\frac{x-z}{x-y}\right) \times 100 \qquad (1)$$

where the positive control represent 100% ROS and the negative control represent 0% ROS. The x, y, and z parameters represent the mean fluorescence signal obtained from the positive control, the negative control, and the samples, respectively.

Lipopolysaccharide (LPS) Stimulation of Whole Blood Samples and Multiplex Cytokine Assay Whole blood samples were collected in ethylenediaminetetraacetic acid (EDTA)-containing Vacutainer™ tubes. The blood was stimulated ex vivo with 100 ng/ml LPS for 24 h at 37° C. Triton X-100 was then added to a final concentration of 0.5% (v/v) and incubated for 10 min at room temperature to lyse the cells. All the samples were centrifuged at 13,200 rpm for 10 min and the serum was separated. Serum levels of cytokines were determined by Bio-Plea Pro Assay (Bio-Rad Laboratories, Hercules, Calif.).

Calibration curves for each cytokine were obtained using the reconstituted standards supplied by the vendor. All assays were carried out directly in a 96-well filtration plate (Millipore, Mass.) at room temperature while protecting the beads from exposure to light. Standards and samples were measured in duplicate and blank values were subtracted from the readings of all samples. In particular, wells were pre-wetted with 100 µl PBS. The beads (~5,000 beads per cytokine) were added along with sample or blank to a final volume of 100 µl in each well and incubated for 30 min at room temperature with continuous shaking. After washing with 100 µl PBS, 25 µl of biotin conjugated detection antibody was added to each well and incubated for additional 30 min. Subsequently, streptavidin-phycoerythrin was added to the wells and incubated for 10 min. After washing-off the unbound streptavidin-phycoerythrin, the fluorescence intensity of the beads (minimum of 50 beads per cytokine) were analyzed in the Luminex 200™ instrument (Austin, Tex.) equipped with Luminex XYP™ platform and Luminex xPONENT™ 3.1 data analysis software.

Statistical Analysis

The results are presented as the mean±S.E.M. (standard error of the mean) and statistical significance between the groups was determined by the unpaired Student's t-test; a p-value of less than 0.05 represents statistical significance between the groups.

FTIR and Miscibility Studies

Differential Scanning calorimetry (DSC) thermal analysis of the samples was conducted at a heating rate of 10° C./min using TA Instruments (Model 2920) differential scanning calorimeter (DSC) calibrated for temperature and enthalpy using indium standard having a melting point of 165.5° C. Samples weighing 7-10 mg were sealed in aluminum hermetic DSC pans using a crimping device. A sealed empty aluminum pan was used as a reference. Nitrogen gas was purged to the unit to maintain an inert atmosphere. The second runs of DSC curves were used to avoid the thermal history. The first DSC run was employed in order to eliminate thermal history. The data from second run DSC is used for further analysis.

Fourier Transform Infrared (FTIR) spectra were obtained at 100° C. For FTIR analysis, the samples were prepared by solution casting on KBr discs using a 5 wt % solution in DMSO. The samples were dried under vacuum at 150° C. for 24 hours to ensure complete removal of any residual solvent. The samples were then stored in desiccators until further use. Infrared measurements were recorded on a FTIR spectrometer (Thermo Scientific Nicolet 380) at a resolution of 4 cm$^{-1}$ averaged over 32 scans. Since each of the components show characteristic affinity towards moisture, care was exercised to minimize the effects of moisture with the aid of a temperature cell by heating the samples to 150° C. and spectra were recorded after equilibrating at 100° C. to assure the absence of moisture and residual solvent.

Results

Quantification of Actual Amount of Genistein in Membranes

Genistein modified PANG and PA:PVP/G membranes were prepared via coagulation induced phase separation by immersing the genistein modified polymer solutions into water bath to form the membranes. The miscibility enhancement via cross-hydrogen bonding between genistein with PA is described below. The present experiment was designed to show whether such specific interaction would be sufficient to retain, if not all, some genistein in the PA membrane during the coagulation process. In order to quantify the amount of potential loss of genistein, the non-solvent bath containing water, genistein, and DMSO was chilled at 15° C. for 96 h to allow the genistein to crystallize and precipitate out from the solution mixture. The precipitate was filtered, dried, and weighed. On the basis of a simple mass balance calculation, i.e., the percent weight loss of genistein=(wt of genistein residue×100)/(wt of PA+wt of genistein in feed), the actual amount of genistein in the final modified membrane was determined.

Figure 4:
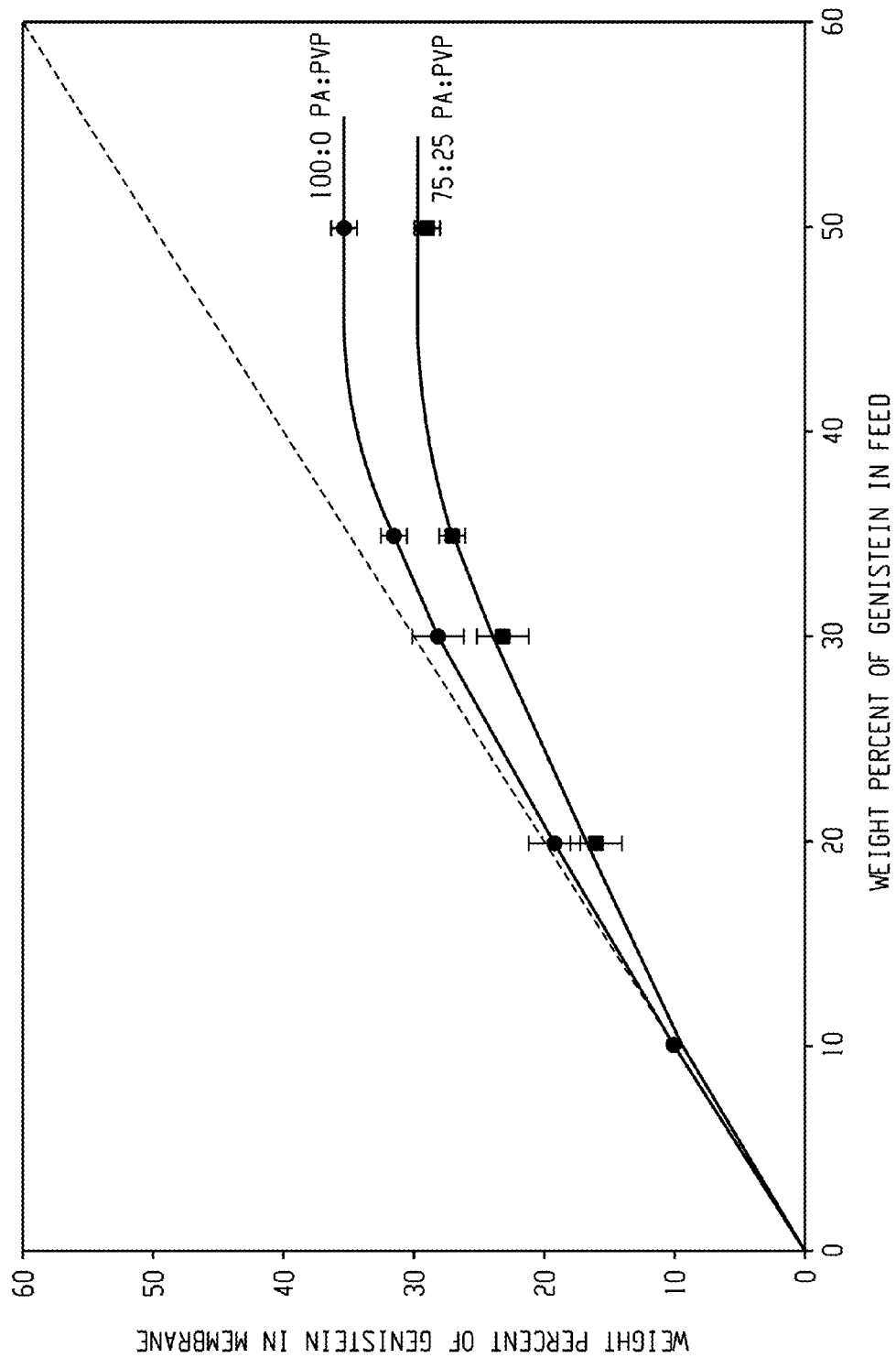
FIG. 4 shows amounts of phytochemical (genistein) retained in a membrane in relation to amount of the phytochemical in the feed solution for two different matrix compositions: 100% PA and 75:25 PA:PVP. The dashed line represents an ideal case representing no phytochemical loss in a non-solvent bath.

As illustrated in FIG. 4, at lower genistein loadings (up to ~30 wt %), most of the genistein added to the feed solution is retained in the final membrane. Beyond about 30 wt % genistein loading, a deviation occurs from the dashed straight line representing the ideal situation, where all genistein in feed were retained in the membrane after coagulation in the non-solvent bath. Upon further increase of genistein concentration (e.g., ~50 wt %), the genistein loading of the final membranes peaked at approximately 35 wt % of the solid content, indicating substantial weight loss during the membrane formation, suggesting that higher loadings are not an advantage. It may be noted that when a similar experiment was performed with mangiferin in place of genistein, the peak loading was apparently somewhat lower. A similar experiment was carried for the PA:PVP/G system. Since PVP and genistein are completely miscible, it was predicted that more genistein might be lost in the water through PVP leaching, which proved to be the case.

Membrane Morphology (SEM)

The surface and cross sectional morphologies of the unmodified and genistein PA membranes formed above were examined by using SEM (FIG. 5). A dense skin layer can be seen on the surface of the unmodified PA membrane (a), whereas cascading finger-like channels developed through the membrane, which are apparent in the cross sectional view. The size of the cascading fingers progressively increases in the thickness direction from the skin layer (i.e., the top layer) where the solvent escapes and the non-solvent enters. It is suggested that the formation of cascading finger-like structures is governed by the changing solvent power at the coagulation front coupled with the hydrodynamic flow of solvent/non-solvent exchange that eventually creates the asymmetric membrane structure. The effects of genistein modification on PA membrane morphology are illustrated in FIG. 5, b-e. A prominent effect of genistein modification is the formation of needle-like genistein crystals that are embedded on the membrane surface even at very low feed compositions of genistein (e.g., 90/10 PA/G, b). As the genistein loading in feed was increased to 80/20 and 70/30 PA/G (c and d) the resulting membranes contained larger seaweed-like crystals (i.e., dense branching morphology) on the membrane surface. Concurrently, the cross sectional morphology of all the modified membranes showed cascading finger-like channels, which were coated with genistein crystals. Increasing the genistein feed composition beyond 30 wt % resulted in the formation of larger incomplete spherulitic crystals on the membrane surface, which are presumably deposited on the surface from the excess genistein (FIG. 5 (e)). Moreover, some needle-like crystals are seen protruding out from the interior surface of the cascading channels. These deposited crystals on the surface can leach out easily upon immersion in non-solvent, especially at 50 wt % genistein loading.

The agreement between the observed crystal morphology at the surface with virtual lack of genistein leaching below 30 wt % implies that these crystals are predominantly segregated to the surface (i.e., the membrane surface as well as the cross-sectional interior surface of the cascading channels), but fully embedded and thus the crystallization presumably prevents leaching of genistein. A similar morphology development can be confirmed in the PA:PVP/G membranes, except that the PVP makes the surface of the membrane more porous, but smoother. The role of genistein crystals at the surface on the anti-oxidant and anti-inflammability properties of genistein modified membranes is discussed below.

Figure 5A:
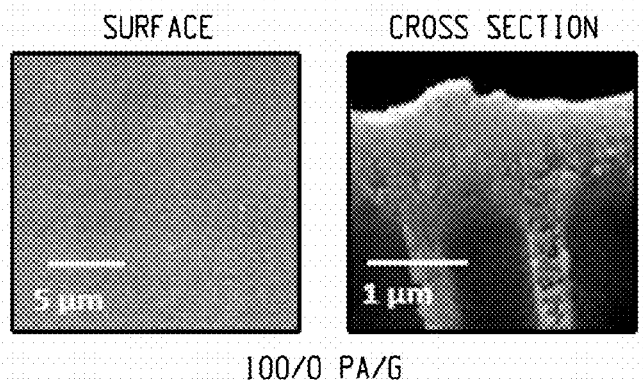
FIG. 5 shows SEM micrographs of the surface (left) and cross sectional (right) morphology of (a) unmodified PA membranes, and genistein modified membranes at (b) a 90/10 PA/G ratio, (c) an 80/20 PA/G ratio, (d) a 70/20PA/G ratio, (e) a 50/50 PA/G ratio, (f) unmodified PES membranes, and g) genistein modified membranes at a 90/10 PES/G ratio. G is used to represent genistein throughout.
Figure 5B:
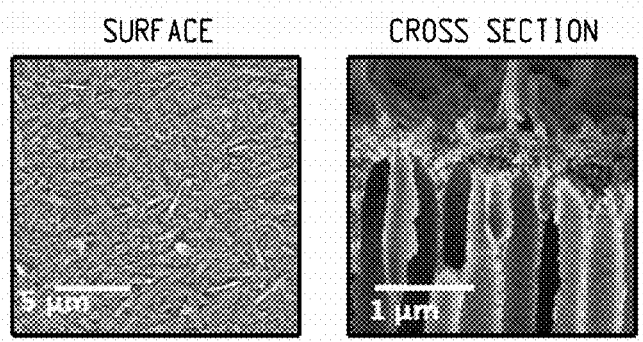
Figure 5C:
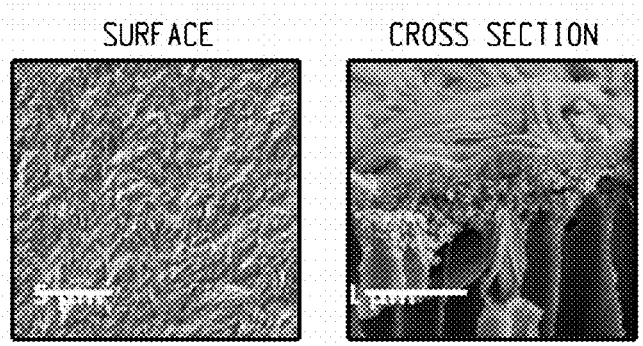
Figure 5D:
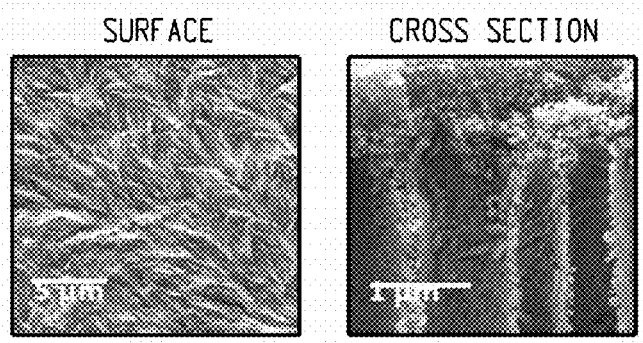
Figure 5E:
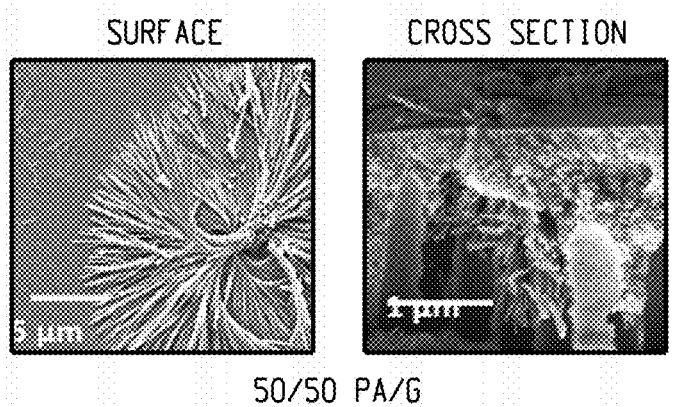
Figure 5F:
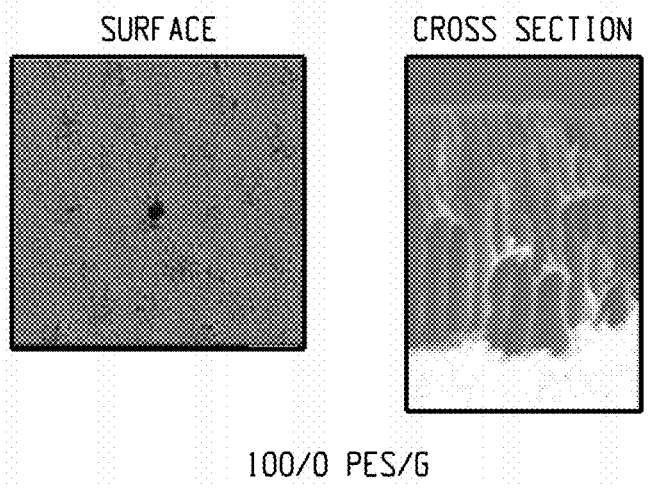
Figure 5G:
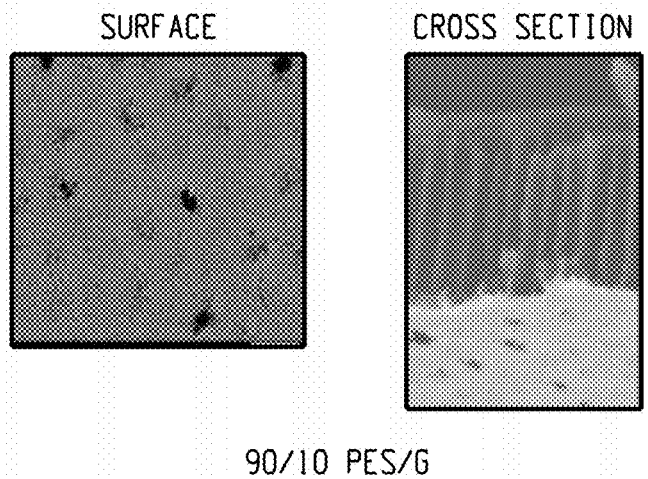

FIG. 5f shows an SEM micrograph of the surface (left) and cross sectional (right) morphology of a PES membrane and FIG. 5g shows results for a PES/G=90/10 membrane. For the unmodified membrane, a dense skin layer can be seen on the surface of the membranes, and the cascading finger-like channels can be seen along the cross section. The size of the cascading fingers progressively increases in the thickness direction from the top of the layer where the solvent escapes and the non-solvent enters. A more porous structure but without genistein crystals is observed on the surface for the PES system than for the PA system.

Cytotoxicity of Unmodified and Genistein Modified Membranes

In addition to performing biocompatibility tests, cytotoxicity testing is performed. In the following described graphs, ratios (such as PA:PVP) are expressed as the relative weights in the feed stock, which may not always reflect the precise percentages in the resulting polymer/membrane.

Figure 6:
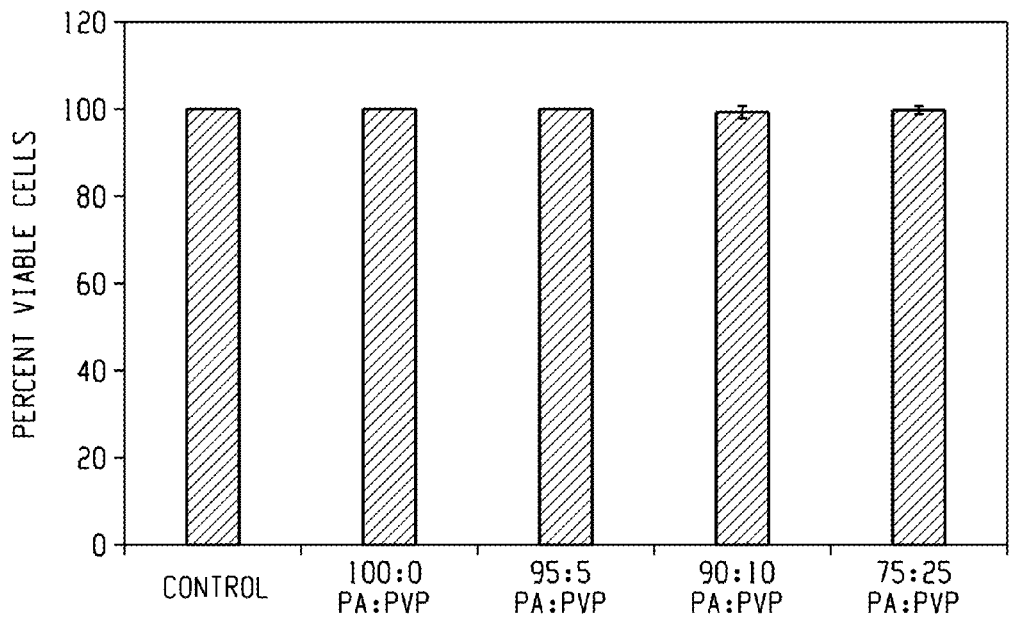
FIG. 6 shows results of cytotoxicity studies conducted with PBMC using PA:PVP membranes showing that cell viability is good for a variety of blends.

As can be seen in FIG. 6, which shows the cell viability for PA and PA/PVP membranes, the unmodified PA membrane exhibits excellent cell viability comparable to that of the control (a conventional hemodialysis membrane). The incorporation of PVP into PA shows the same cell viability without any harmful effect.

Figure 7:
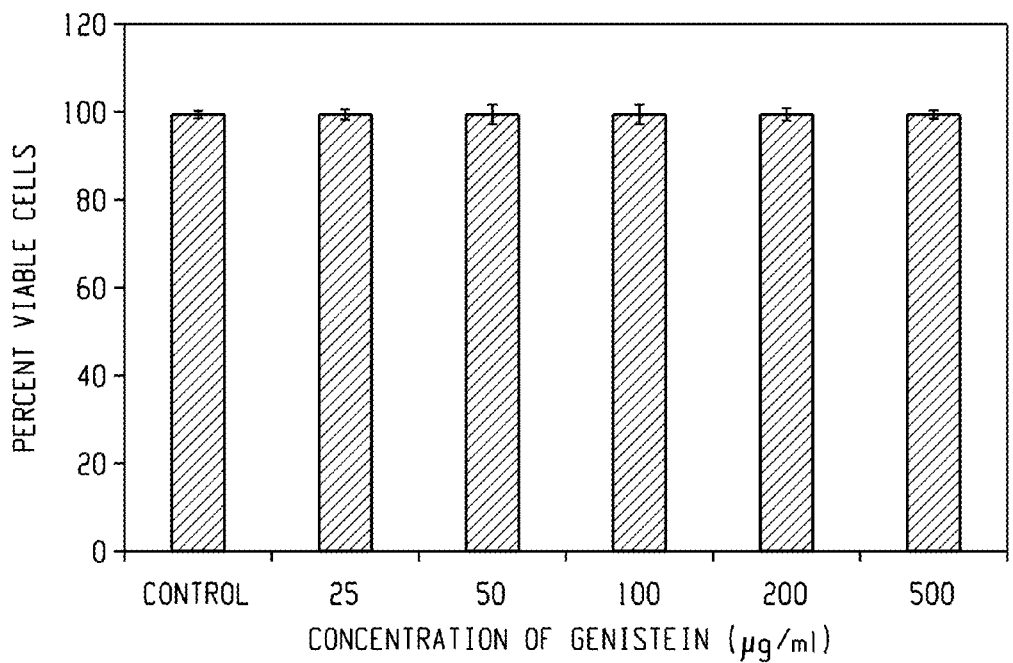
FIG. 7 shows results of cytotoxicity studies conducted with PBMC using pure genistein at different concentrations, showing that showing that cell viability is good for all concentrations tested.

FIG. 7 demonstrates the cell viability results of the pure genistein, which clearly reveals that pure genistein is non-cytotoxic to the PBMC in the entire concentration range of the assay (25-500 µg/ml). In principle, any modifying agent intended for medical device applications must be non-cytotoxic in its pure form as well as when bound to a substrate (either physically or chemically). These findings establish a basis for the selection of genistein towards subsequent development of the functional hemodialysis membranes for suppressing DIOS and MII.

Cytotoxicity studies were extended to genistein modified PA/G and PA:PVP/G membranes. Although not shown, the results demonstrate that both PA/G as well as PA:PVP/G membranes exhibit exceptional cell viability (as good as the control). It was estimated that the genistein loading in these modified membranes (PA/G and PA:PVP/G) ranged between 100-200 µg/cm$^2$ of membrane area. Although the cytotoxicity results of pure genistein as well as both PA/G and PA:PVP/G membranes are very promising, it should be cautioned that passing the cytotoxicity test is regarded merely as a minimum necessary criterion.

DHR Assay with Unmodified Polymer Membranes

Figure 8:
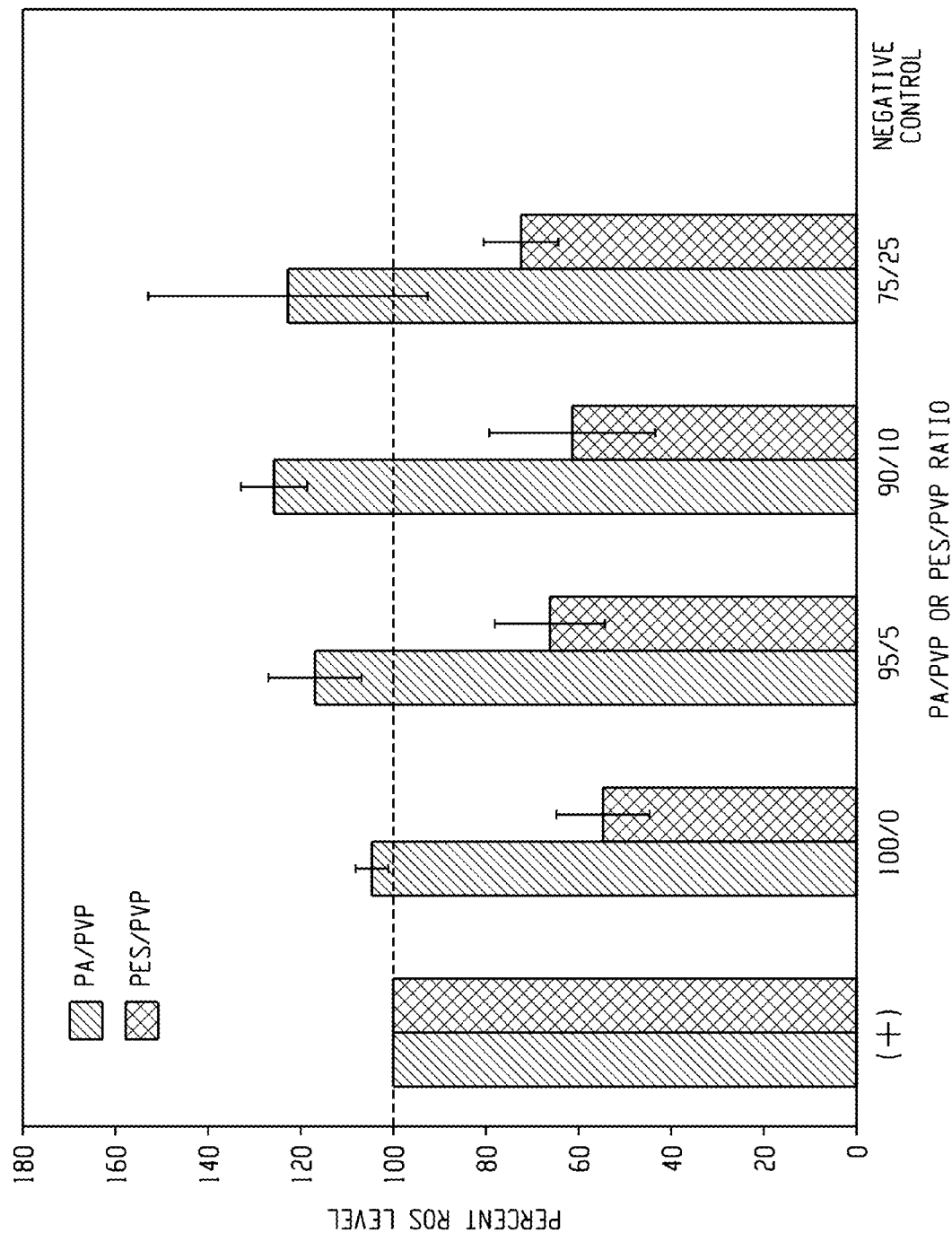
FIG. 8 shows DHR assay results as % ROS level for unmodified PA and PA:PVP membranes, and for unmodified PES and PES:PVP membranes.

The outcome of oxygen radical generation (% ROS) due to blood contact with unmodified PA:PVP membranes was studied. The membranes were incubated for 3 h at 37° C. in order to simulate hemodialysis conditions. Results of DHR assays performed with unmodified membranes fabricated with 100:0, 95:5, 90:10 and 75:25 PA:PVP and PES:PVP ratios are shown in FIG. 8. ROS levels of the membrane samples (blood+PBS+membrane+DHR+PMA) were compared with that of the positive control (blood+PBS+DHR+PMA) to determine statistical significance. Values shown are mean±S.E.M obtained from three experiments (n=3).

In order to calculate 'p' value to establish statistical significance, the mean fluorescence values of the membrane samples were compared with that of the positive control. It can be noticed that the blood contact with unmodified membranes has lead to an increase in the ROS level. For example, in the 90:10 PA:PVP membrane, the increase in ROS level was found to be as high as 30% compared to that of the positive control.

This result is significant for hemodialysis, because typical hemodialysis patients' blood comes in contact with the membrane approximately 3-4 h/session and 3-4 sessions/week. It is suggested that when blood comes into contact with the synthetic polymer surface, the neutrophils are activated leading to oxidative burst and the oxidative stress builds up in the patient's body. The body quickly neutralizes these radicals by natural anti-oxidant molecules such as superoxide dismutase and glutathione peroxidase. Such a defense mechanism is generally deficient for HD patients and thus, over a period of time, the excessive production of oxygen radicals overpowers the natural anti-oxidant defense mechanism and thus eventually leading to dialysis induced oxidative stress (DIOS). The effect of PVP on ROS levels showing the rise in ROS with increasing PVP concentration in the membrane (FIG. 8) is contrary to the general perception that addition of hydrophilic polymer to hydrophobic polymer improves biocompatibility of the membranes. In general, hydrophobic polymer surfaces are known to be good adhesion promoters with strong protein adsorption capability, but they are poor complement activators. The reverse is true for hydrophilic polymers that show poor protein adsorption, but are strong complement activation. Therefore, it is generally accepted that an optimum surface for blood contact must be made up of hydrophobic/hydrophilic polymer blends. However, in terms of oxygen radical generation, the results obtained suggest that the addition of PVP to PA raises the ROS levels in blood.

In the case of PES, the unmodified PES membrane reduced ROS level, by about 40%, as compared to the control, and adding PVP into the PES membranes did not increase the ROS levels as much as in the case of the PA/PVP membranes. One reason for the ability of PES to cause ROS reduction may be because PES does not stimulate the neutrophils in the blood to produce the ROS.

Anti-Oxidant Properties of Pure Genistein and Genistein Modified Membranes

Figure 9:
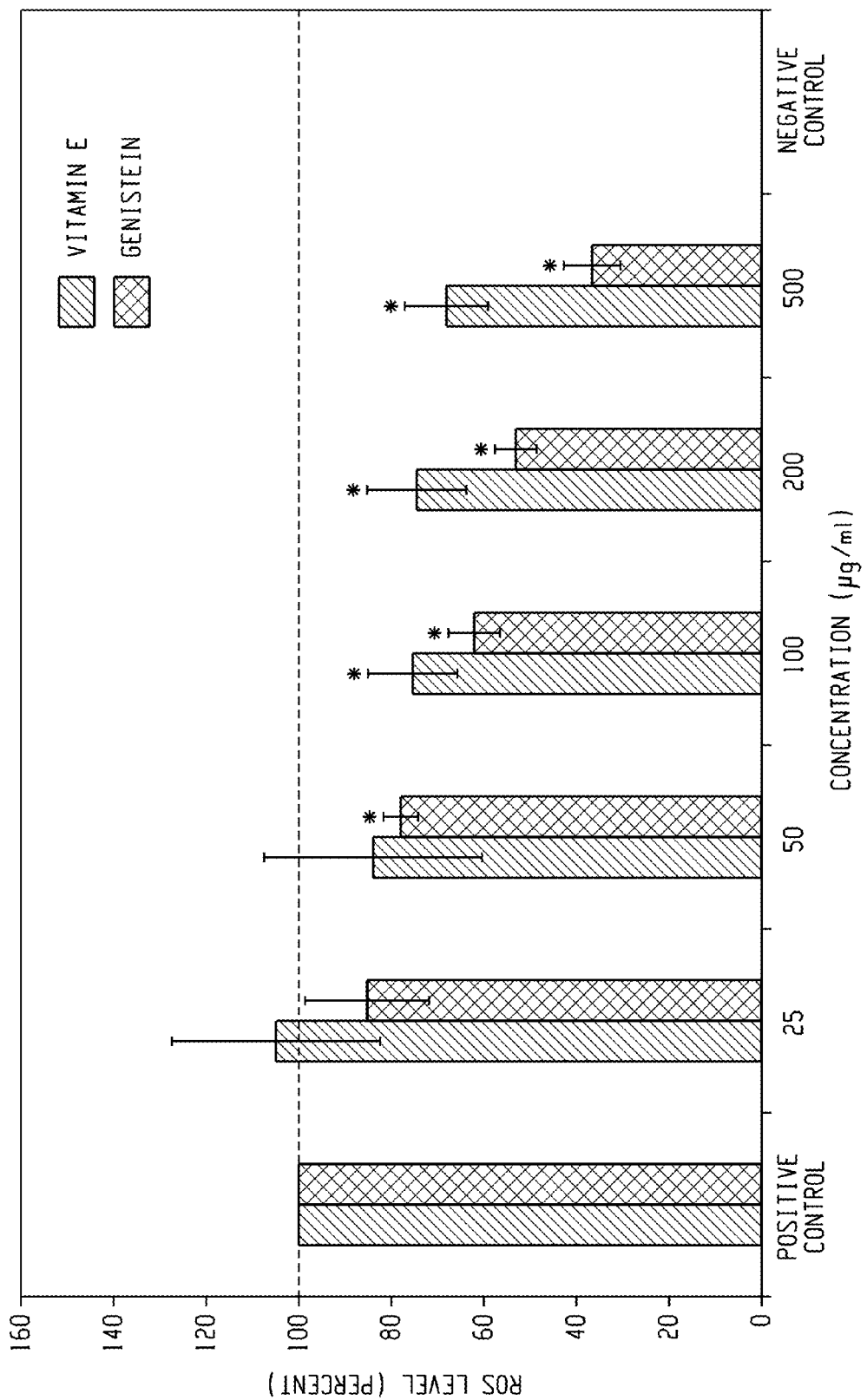
FIG. 9 shows DHR assay results as % ROS level for pure antioxidant (vitamin E or genistein).

DHR assays executed with pure genistein (25-500 µg/ml) were performed The results of ROS levels obtained with pure genistein (in DMSO) are shown in FIG. 9, which shows results for Vitamin E for comparison. Values shown are mean±S.E.M. obtained from three experiments (n=3). ROS levels of the genistein/Vitamin E samples were compared with that of the positive control to determine statistical significance, which is represented by asterisks (*). These results clearly demonstrate the anti-oxidant properties of genistein as observed by the dose-dependent reduction of ROS level.

It can be seen from the results that genistein is able to suppress ROS levels significantly, even at concentrations as low as 25 µg/ml and that the suppression of ROS occurs in a dose-dependent manner, i.e., higher concentration of genistein results in greater suppression of ROS levels. Suppression is greater than for Vitamin E.

The cell viability results described above, combined with anti-oxidant properties of genistein displayed in FIG. 9, attest not only to the safety of genistein to the blood cells, but also its efficacy as an anti-oxidant.

Figure 10:
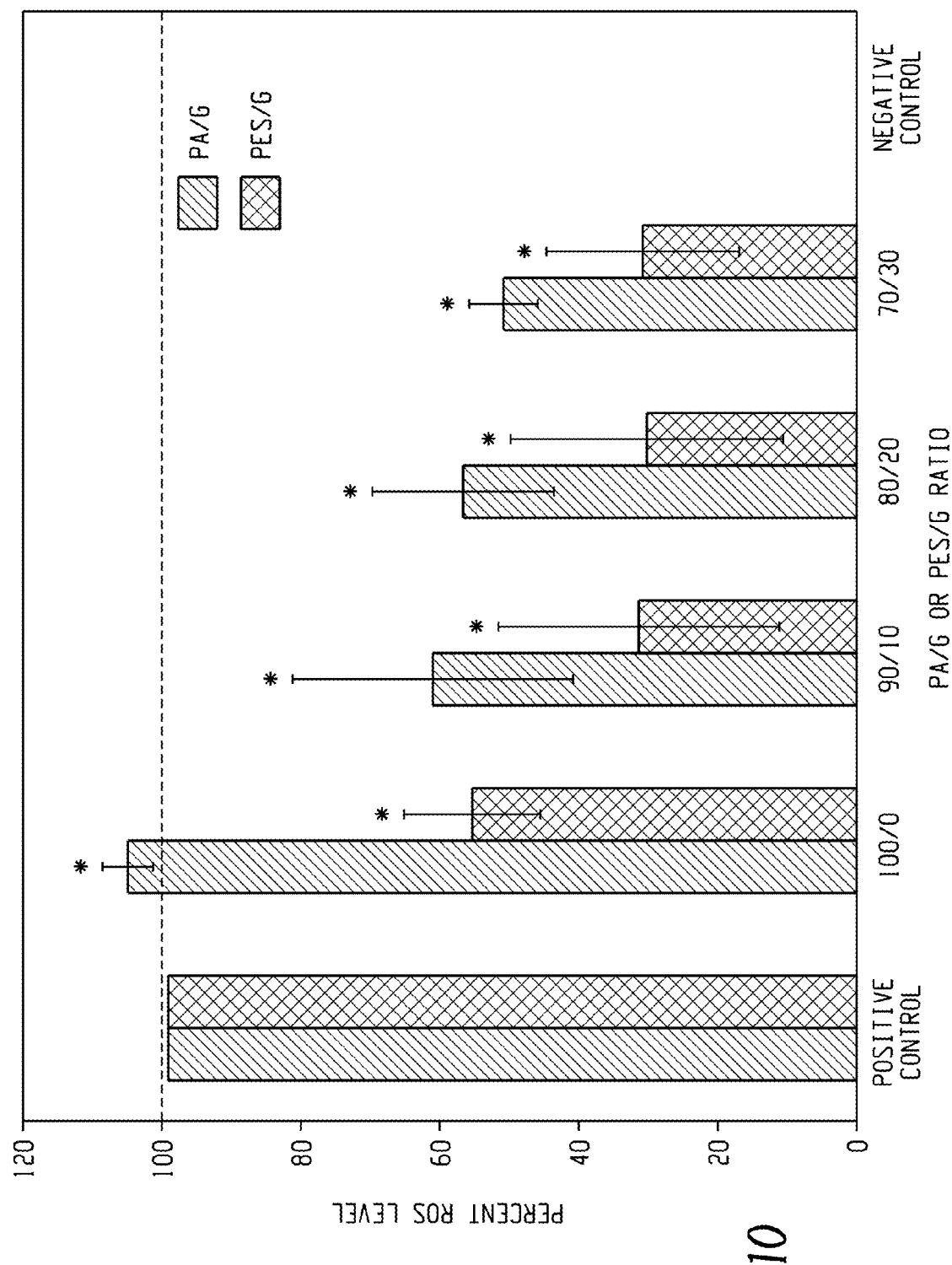
FIG. 10 shows % ROS level for PA/G and PES/G membranes.
Figure 11:
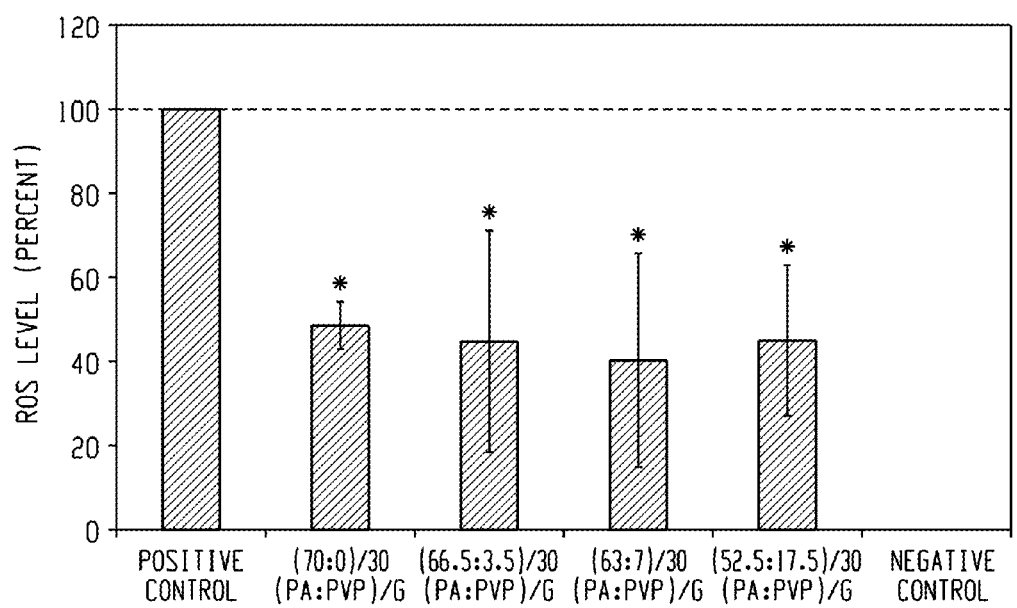
FIG. 11 shows % ROS level for PA:PVP/G membranes.

The ROS levels of the genistein modified PA/G PES/G and PA:PVP/G membranes measured by DHR assay after 3 h incubation 37° C. are shown in FIGS. 10 and 11, which show a dose-dependent suppression of oxygen radicals. Values shown are mean±S.E.M. obtained from three experiments (n=3). Asterisks (*) represent statistical significance in comparison with positive control.

Whereas the unmodified PA membrane shows a slight increase in oxygen radicals, with the addition of genistein to the PA membrane, the ROS level was reduced by about 50% in the case of the 70/30 PA/G feed composition. This 50% reduction of the oxygen radicals is close to that of the pure genistein shown in FIG. 9. However, no ROS test was performed with PA/G above 30% because a usable film could not be formed above a genistein concentration of 50 wt %; in fact the film became very brittle and crumbled. It should be borne in mind that most genistein crystals are segregated to the surface of the membrane as well as of the cascading channels at least at the low loading level of up to 30 wt % (FIG. 5) without significant leaching. On the basis of the observed suppression of ROS of the 70/30 PA/G membrane comparable to that of the genistein/DMSO solution, it may be concluded that almost all genistein is accommodated at the membrane surface/pore interface of the PA/G membranes. As demonstrated earlier, the surface-segregated genistein crystals may help in the improvement of the anti-oxidant properties of the genistein modified membranes.

Not all genistein molecules with the crystals are exposed at the membrane surface, and thus the contribution to the observed improvement of the anti-oxidant properties it is unexpected. Additionally, the DHR assay works on the principle of detecting the intracellular response and thus, without any significant genistein leaching, there should be no intracellular response. Without being fully understood, the unexpected results may be reconciled as follows. Given the high mobility of the intracellular and extracellular radicals, it is possible that these radicals may move from one environment to another. When neutrophils or PBMC come in contact with the surface segregated genistein crystals, the radicals in the extracellular environment can be transported to the phenolic group of the genistein molecule at the crystal surface. These radicals abduct the protons from the phenolic group of genistein and are thus neutralized. The genistein molecule in turn is stabilized via resonance stabilization. Moreover, these radicals can be transferred from one genistein molecule to another within the crystal, therefore not all genistein crystal molecules have to be in direct contact with the blood cells to promote the radical scavenging process. It may be hypothesized that the mobile radicals that are transported to the phenolic group of the genistein molecule are responsible for the observed ROS suppression with or without significant genistein leaching.

FIG. 10 compares the ROS levels of the PA/G and PES/G genistein modified membranes. A dose-dependent suppression of the ROS levels is observed. The modified PES membranes performed better than the modified PA membranes. Genistein-modified PES membranes were shown to reduce the ROS levels by about 70% in all cases.

The effects of PVP addition on the anti-oxidant properties of PA:PVP/G membranes are shown in FIG. 11. Since the 70/30 PA/G sample showed the best ROS reduction, the genistein content for the PA/PVP/G studies was maintained at 30%; i.e., only the ratio of PA to PVP was varied. All samples show an impressive ROS reduction of 40~50%. It can therefore be assumed that for PA/PVP/G ternary systems, the membrane ROS suppression is largely controlled by the genistein dosage.

Comparison studies between genistein and mangiferin modified PA membranes similarly formed (results not shown) suggest that genistein is superior to mangiferin with respect to its effect on % ROS.

In experiments performed with a combination of genistein and glucose, without polymer, glucose was found to reduce the beneficial effect of genistein on ROS, suggesting that addition of glucose groups to the flavone or isoflavone backbone may not be beneficial.

Effect of Genistein Modified Membranes on Serum Cytokine Levels

Figure 12:
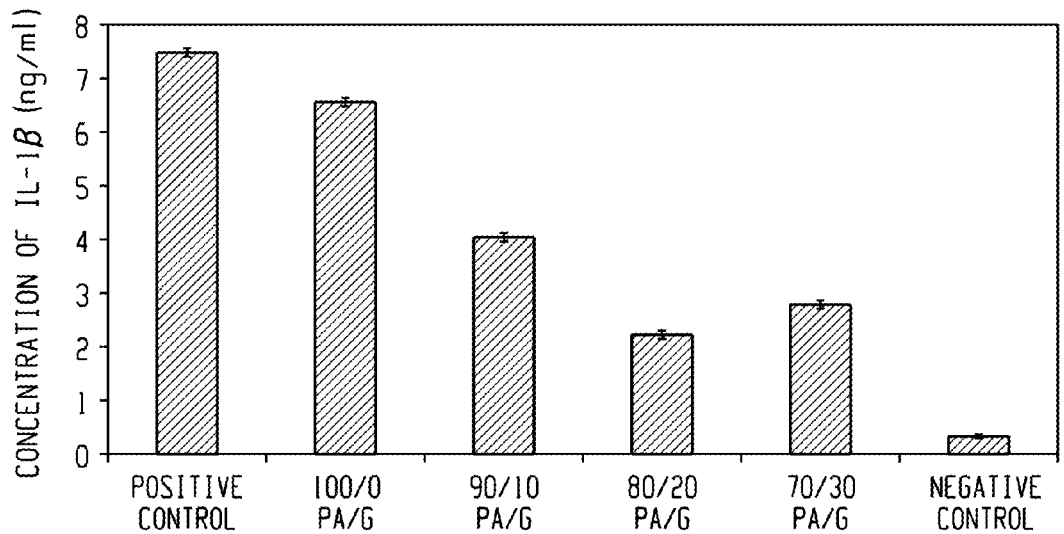
FIGS. 12 and 13 show serum levels of IL-1β measured after incubating LPS stimulated whole blood for 24 h with PA/G membranes and PA:PVP/G membranes, respectively.
Figure 13:
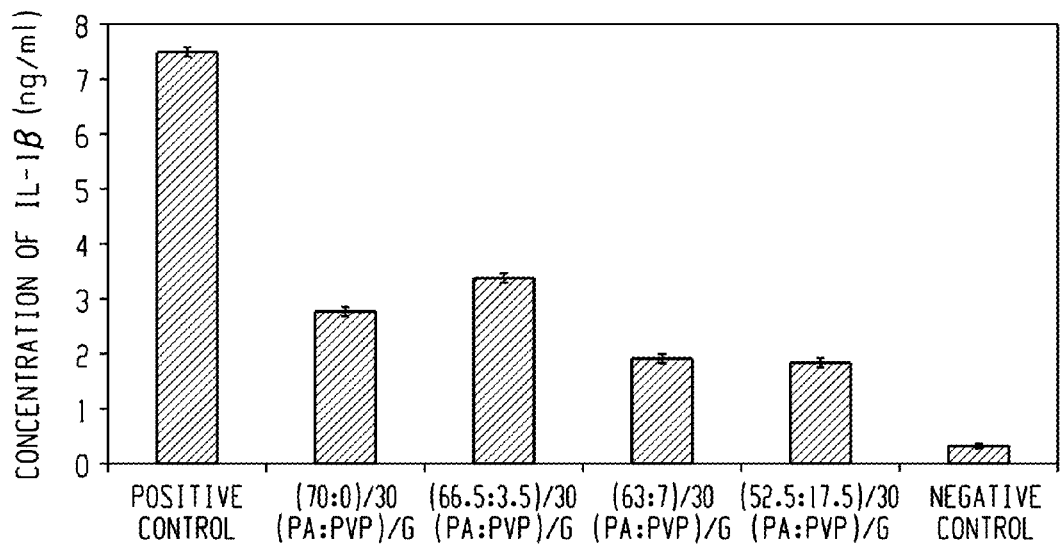

Although the effect of genistein modification of the polymer membrane on the cell viability and the ROS suppression appears advantageous, another aspect of interest in the case of a biocompatible polymer is the effect of genistein modification on the anti-inflammatory properties. In this experiment, the concentration of pro-inflammatory cytokines, such as IL-1β, IL-6, and TNF-α in serum, were measured by a Luminex flow cytometer after ex vivo stimulation of the whole blood with LPS. These cytokines were chosen because it has been clinically demonstrated that the elevated levels of IL-1β, IL-6 and TNF-α in serum of ESRD patients are closely correlated with increased mortality risk. These cytokines have been suggested to cause fever during hemodialysis, reduced blood pressure, and anemia in long-term hemodialysis patients. The effect of PA/G and PA:PVP/G membranes on serum levels of IL-1β are shown in FIGS. 12 and 13. In these plots, the positive control represents the whole blood stimulated with LPS, sample tubes contained LPS stimulated blood incubated with various PA/G (or PA:PVP/G) membranes (2×0.4 $cm^2$ discs of 100/0, 90/10, 80/20 and 70/30 PA/G) whereas the negative control represents the whole blood without the LPS stimulation. Values shown are mean±S.E.M. obtained from two experiments (n=2).

As can be seen in FIG. 12, the unmodified membranes (i.e., 100/0 PA/G) slightly suppressed IL-1β secretion from PBMC. With the addition of genistein, the suppression of IL-1β secretion from PBMC is more pronounced, even at fairly low genistein loading (i.e., 90/10 PA/G). In order to determine the effect of PVP addition on these PA/G membranes, samples were prepared with a fixed genistein composition of 30 wt %; only the PA:PVP ratio was changed systematically. As shown in FIG. 13, there was a slight increase in IL-1β concentration at a very low PVP concentration (66.5: 3.5/30 PA:PVP/G). However, with further increase of PVP content, progressive suppression of IL-1β was realized.

Figure 14:
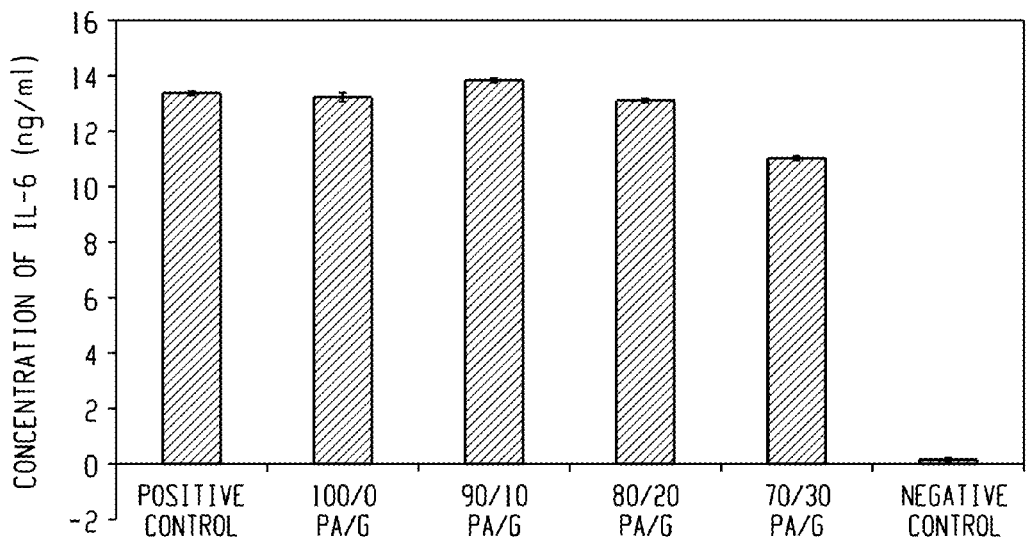
FIGS. 14 and 15 show serum levels of IL-6 measured after incubating LPS stimulated whole blood for 24 h with PA/G membranes and PA:PVP/G membranes, respectively.
Figure 15:
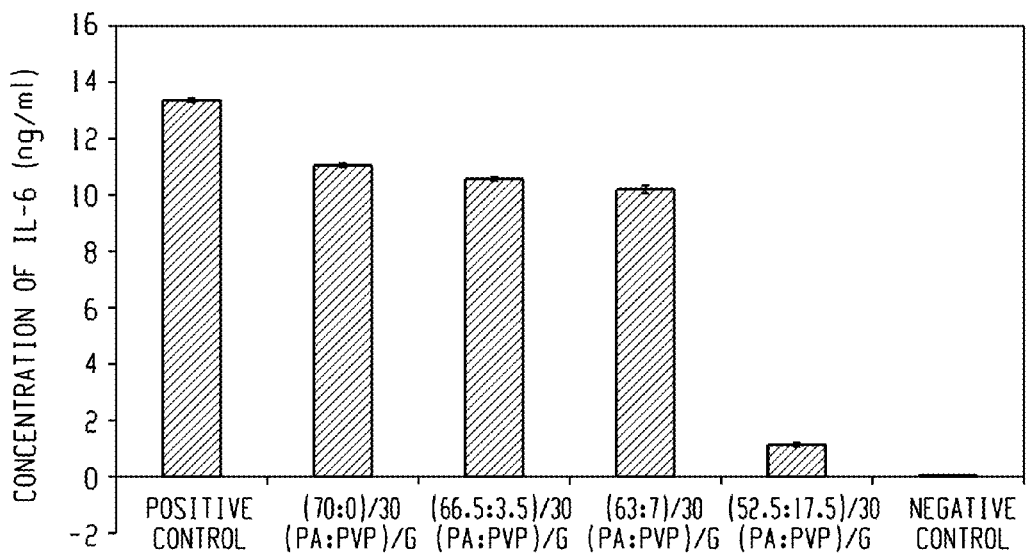

Similar tests were performed for IL-6 and TNF-α (FIGS. 14-17). In the case of IL-6, the unmodified membranes (100/0 PA/G) produced virtually no change in serum concentration (FIG. 14). Unlike the case of IL-1β, only the higher genistein loadings (70/30 PA/G) were effective in producing a reasonable decrease in IL-6 concentration. On the other hand, the addition of PVP reduced the IL-6 level at lower PVP compositions, whereas a sudden drop in IL-6 was noticed at a higher PVP composition (e.g., 52.5:17.5/30 PA:PVP/G) (FIG. 15).

Figure 16:
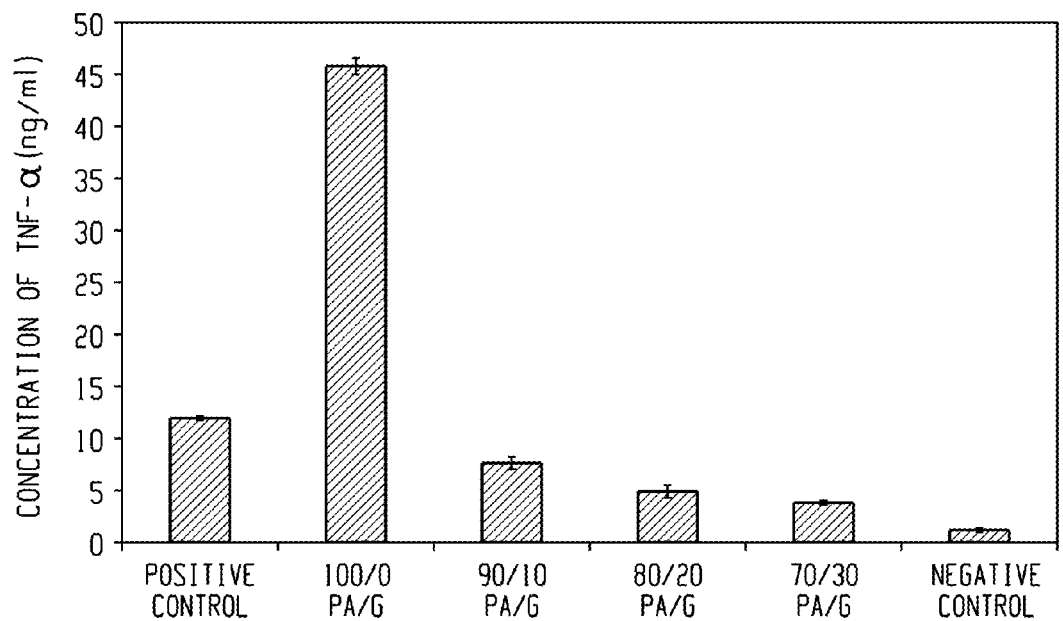
FIGS. 16 and 17 show serum levels of TNF-α measured after incubating LPS stimulated whole blood for 24 h with PA/G membranes and PA:PVP/G membranes, respectively.
Figure 17:
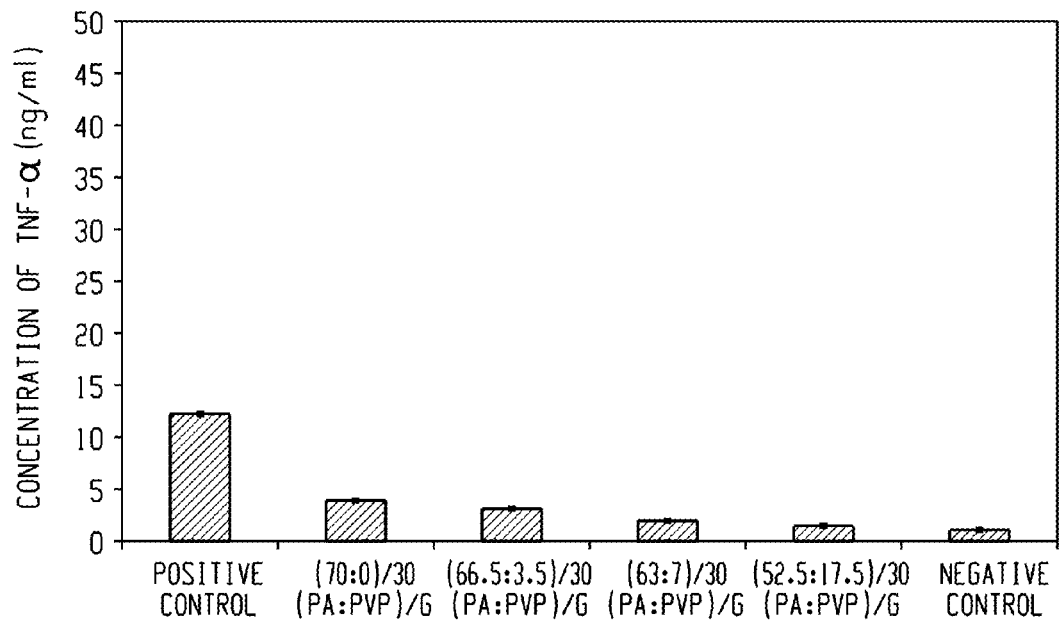

FIGS. 16 and 17 show the results for TNF-α with PA/G and PA:PVP/G membranes. Among the three cytokines measured, the unmodified PA and PVP membranes produced the largest increase in the concentration of TNF-α, as shown in FIG. 16 (i.e., almost 4 times increase as compared to the positive control). Upon adding genistein to these membranes, a dramatic suppression of TNF-α concentration can be seen, even at a relatively low genistein loading (for example 90/10 PA/G), which indicates the outstanding anti-inflammability property of these genistein modified membranes. Further increase in genistein composition in the PA/G membranes further reduced TNF-α level in serum drastically, i.e., close to the negative control. It is noted that, with the addition of PVP to the PA/G membranes, the TNF-α level is suppressed progressively and approaches that of the negative control (FIG. 17).

In a comparison study with mangiferin (results not shown), PA/G and PA:PVP/G membranes were found to be superior to those with comparable amounts of mangiferin in suppression of IL-1β secretion, particularly at higher levels of the antioxidant. IL-6 suppression was also superior for the genistein—modified PA and PA:PVP membranes than for mangiferin ones, particularly, at higher PVP concentrations TNF-α levels were also lower for PA/G and PA:PVP/G than for comparable PA/M membranes.

Figure 18:
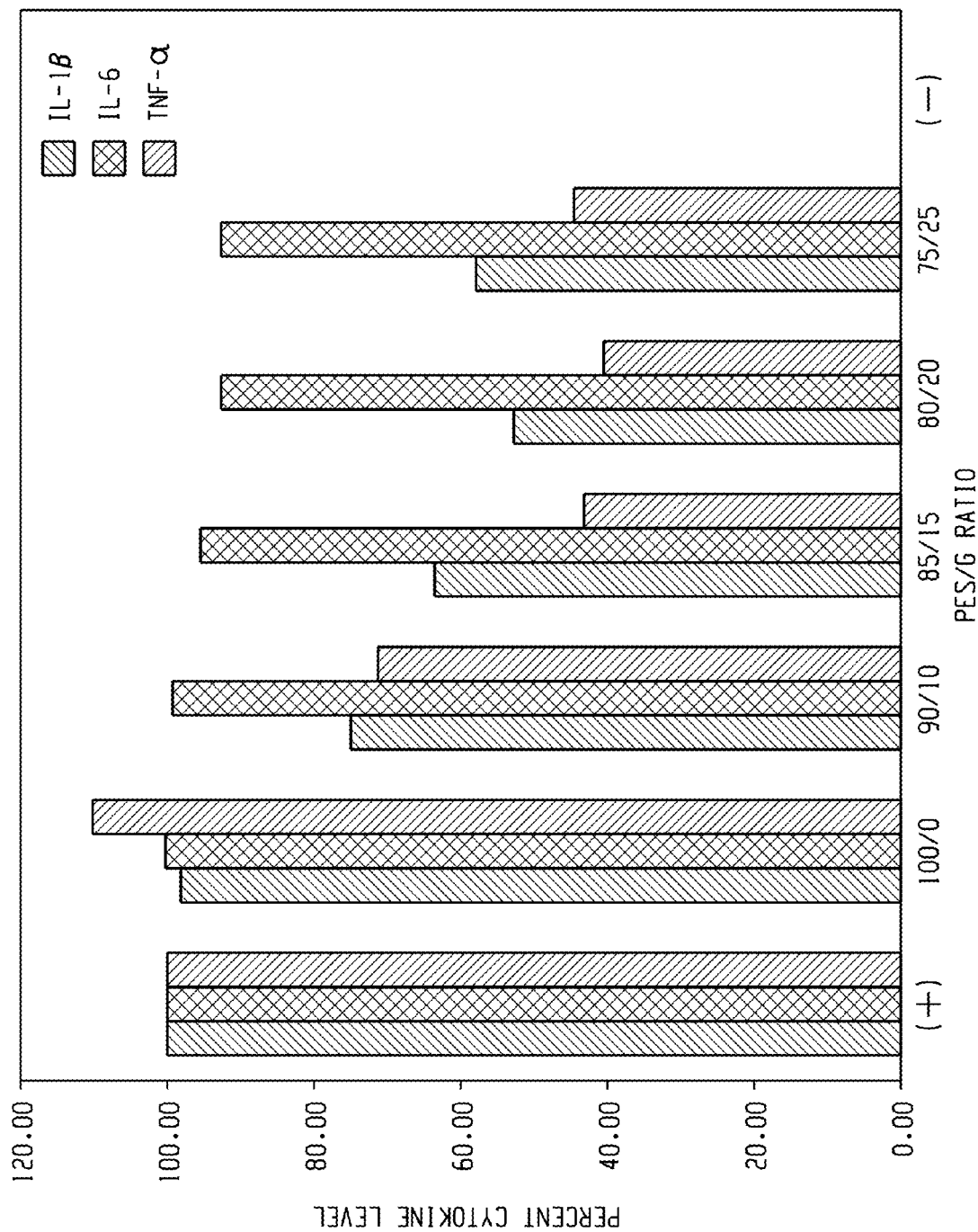
FIG. 18 shows serum levels of cytokines measured after incubating LPS stimulated whole blood for 24 h with PES/G membranes.

FIG. 18 shows analogous results for PES/G membranes, where all three cytokines are reduced, although IL-6 only modestly, as compared with the control.

As previously noted, hydrophilic polymers that contain charged groups strongly activate the complement system whereas hydrophobic polymers show less complement activation. It can be argued that the negligible or virtually no increase in IL-1β and IL-6 concentration (in comparison to the positive control) observed with pure PA membranes (i.e., 100/0 PA/G) could be attributed to poor complement activation by PA, which in turn is dictated by the extreme hydrophobicity of these unmodified membranes. However, the dramatic increase of TNF-α by the PA membranes could not be answered solely based on complement activation. It has been shown that blood contact with synthetic polymer surface triggers the secretion of IL-1, which in turn promotes TNF-α secretion by monocytes. Therefore, the paracrine signaling function of IL-1 might have contributed to the observed increase in TNF-α concentration by the unmodified PA membranes. It is suggested that the surface crystallization of genistein at the pore interface has contributed not only to the improvement of anti-oxidant property, but also the anti-inflammability property of the genistein modified membranes.

Mechanistically, it has been previously demonstrated that cytokine secretion due to LPS stimulation of human monocytes requires the activation of protein tyrosine kinase and protein kinase C (PKC), prior to gene transcription. Genistein has been shown to suppress IL-6 production in a dose-dependent manner, which has been attributed to its inhibition of protein tyrosine kinase. Similarly, other in vitro experiments have also demonstrated the ability of genistein to significantly suppress serum concentration of IL-16 and TNF-α following LPS stimulation of blood. Therefore, it can be concluded that the ability of genistein to inhibit protein tyrosine kinase is responsible for the observed suppression of all three cytokines by PA/G membranes. Moreover, the incorporation of PVP (i.e., PA:PVP/G membranes) has resulted in the reduction of all the three cytokines. Although PVP is a hydrophilic polymer, it does not contain any charged groups to activate the complement cascade that promotes cytokine secretion, which may account for the general perception that PVP addition results in improved biocompatibility of conventional HD membranes.

FTIR and Miscibility

Infrared spectroscopy exploits the fact that PA, PES, and PVP have specific frequencies at which they rotate or vibrate corresponding to discrete energy levels (vibrational modes). By measuring at a specific frequency over time, changes in the character or quantity of a particular bond can be measured.

Figure 19:
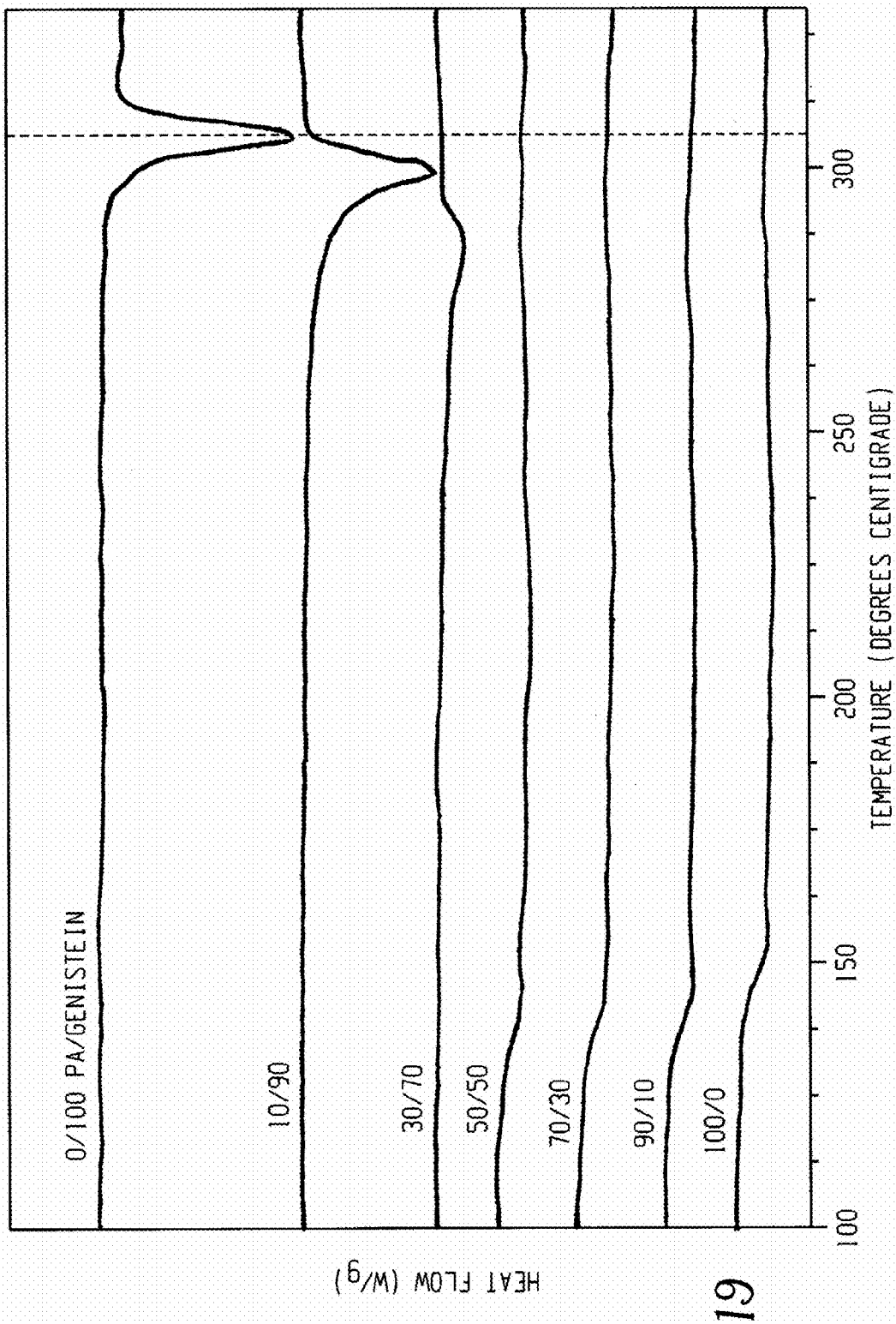
FIG. 19 shows DSC thermograms of PA/genistein blends demonstrating melting point depression of genistein due to PA addition and Tg suppression of PA due to incorporation of genistein.

FIG. 19 shows DSC thermograms of PA/genistein blends demonstrating melting point depression of genistein due to PA addition and $T_g$ suppression of PA due to incorporation of genistein. There is a depression of $T_g$ of PA due to the addition of genistein and the melting point of genistein is depressed due to the addition of PA. Further genistein can be incorporated into PA up to 50 wt % in the amorphous state.

Figure 20:
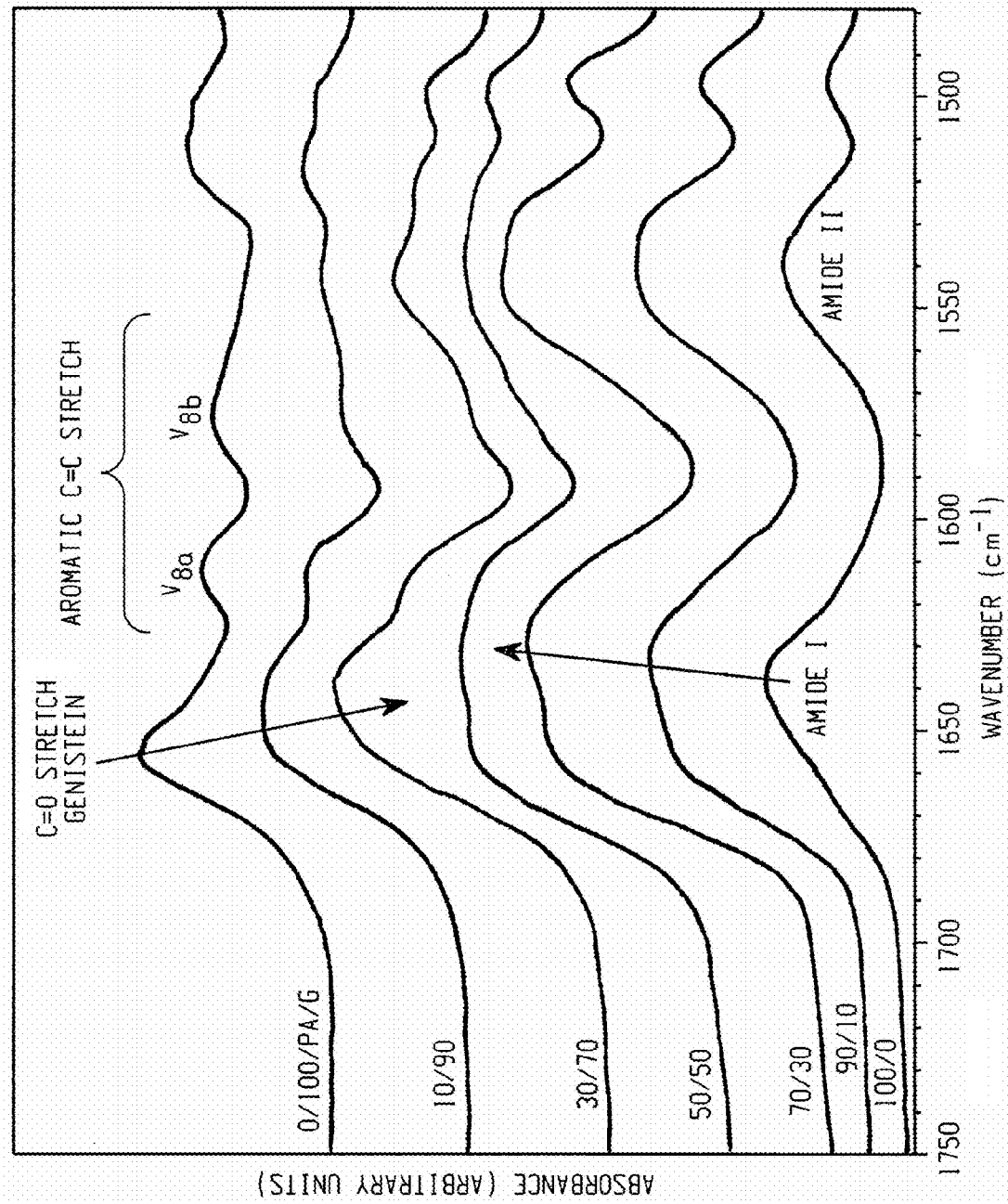
FIG. 20 shows the FTIR spectra recorded at 100° C. of PA/genistein blends in the 1500-1800 $cm^{-1}$ range. It should be noted that both PA and genistein are self-associating. The plot demonstrates hydrogen bonding formation as shown by the systematic movement of amide I band of PA and carbonyl band of genistein to lower frequencies
Figure 21:
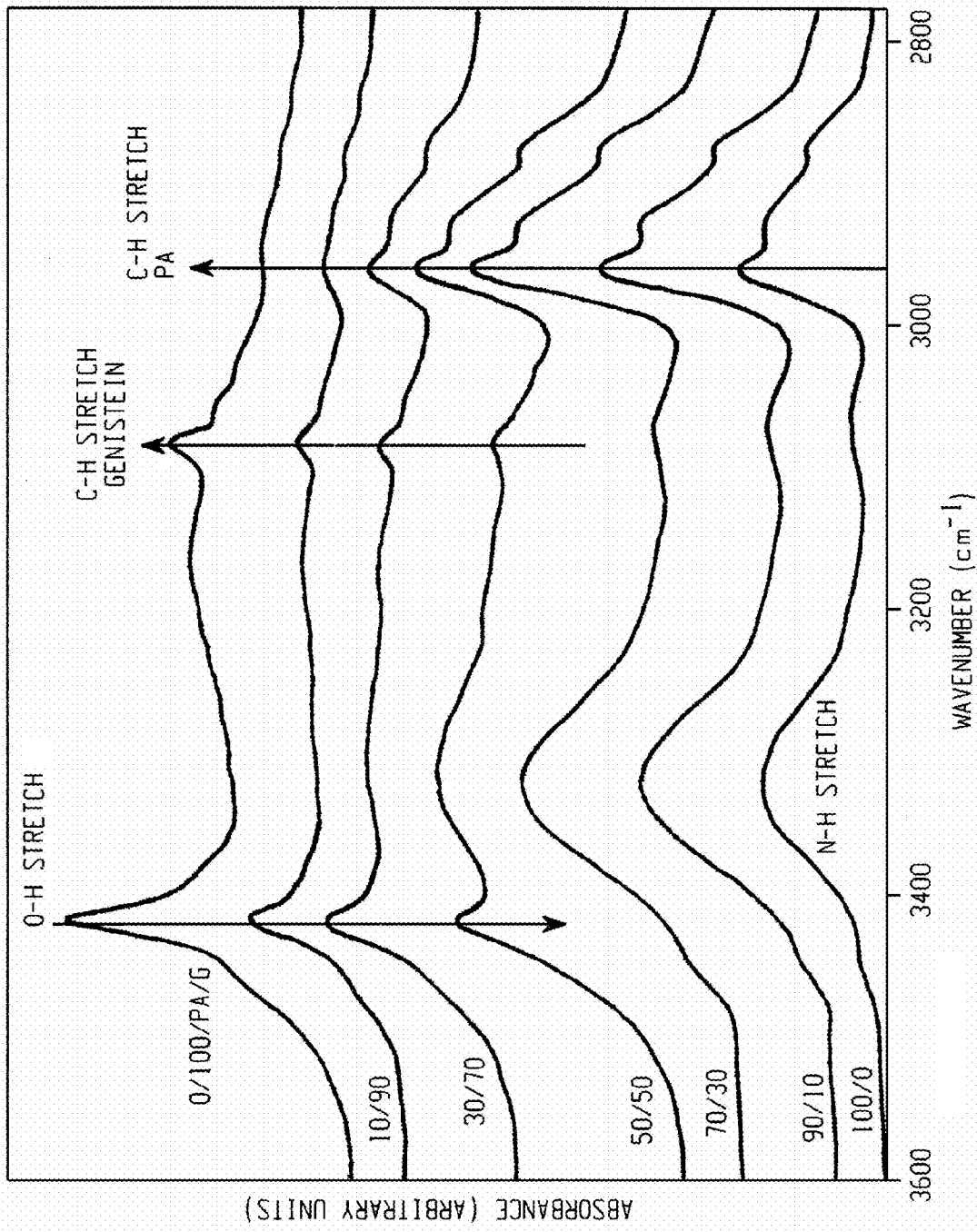
FIG. 21 shows the FTIR spectra recorded at 100° C. of PA/genistein blends in the range of 2700-3600 $cm^{-1}$. Explicit C—H stretching bands corresponding to genistein and PA and a sharp O—H stretching band for genistein can be observed.

FIG. 20 exhibits the FTIR spectra of PA/genistein blends recorded at 100° C. in the 1500-1800 cm$^{-1}$ range and FIG. 21 shows FTIR spectra for PA/genistein blends in the 2700-3600 cm$^{-1}$ range. It should be emphasized that both PA and genistein are self-associating components, capable of performing intra-molecular hydrogen bonding. In general, the shift in band due to hydrogen bonding can occur under the following scenarios. A band shifts towards higher frequencies when hydrogen bonds are released. On the other hand, shift towards lower frequency occurs due to formation of newer hydrogen bonds. The second aspect contributing to the movement of bands is the strength of hydrogen that is released compared to the strength of hydrogen bonds that are newly formed. So, the competition between intra-molecular hydrogen bonding and inter molecular hydrogen bonding combined with the strength of various possible interactions results in the peak shift that is observed in typical IR spectrum. The addition of genistein, the amide I band of PA exhibits a relatively appreciable shift to lower frequencies due hydrogen bonding with the hydroxyl groups of genistein. In contrast, the aromatic C=C band does not show any movement since it is not involved in any specific interaction. The assignments $v_{8a}$-$v_{8t}$ represent the C=C ring stretching vibrations that is characteristic of six-membered heterocyclic ring (for example benzene). However, unlike benzene, these pairs are not degenerate in phenyl compounds. The addition of genistein to PA also causes the amide O band to split into two bands. The band at higher frequency might correspond to the release of intra molecular hydrogen bonds existing between the amide groups whereas the frequency at lower frequency may be due to the formation of cross hydrogen bonding interactions occurring between amide groups of PA and hydroxyl and carbonyl groups of genistein.

It is more difficult to analyze band movements in the N—H stretching region due to the overlap of O—H and N—H stretching bands. It is of interest to note the sharpness of the O—H stretching peak in case of genistein (FIG. 21). In genistein, the degree of intra-molecular hydrogen bonding less significant as the hydroxyl groups are sterically hindered. This results in a sharp band for hydroxyl stretching. Upon mixing, the carbonyl bands of both genistein as well as PA shift to lower frequency suggesting the occurrence of cross hydrogen bonding interactions between the two entities. The possible interactions, in these blends include N—H . . . C=O (self), N—H . . . C=O (cross), C=O . . . O—H (cross) and N—H . . . O—H (cross).

Figure 22:
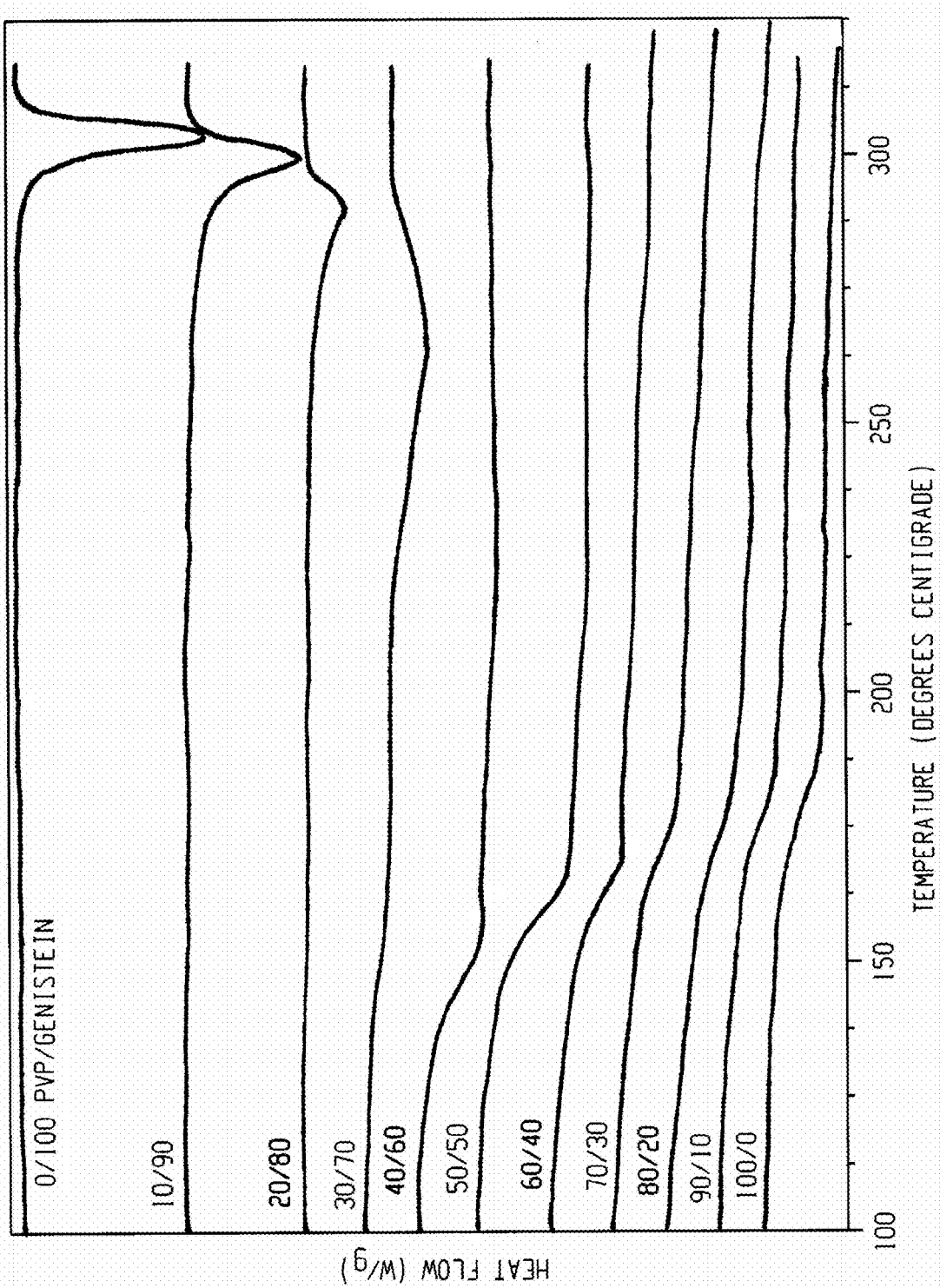
FIG. 22 shows second run DSC thermograms of PVP/genistein blends showing appreciable melting point depression and also low temperature shift of Tg of the blends.

DSC thermograms of PVP/genistein samples showed a single Tg. However, Tg of PVP/genistein blends consistently shifted to lower temperatures with increasing genistein concentration (FIG. 22). No liquid-liquid phase separation was observed in the entire composition range, but large spherulitic structures developed at higher genistein concentrations signifying the isotropic liquid+crystal coexistence regions. It can be clearly seen that there exists a significant depression of melting point of PVP/genistein blends and in addition, the isotropic+crystal transition occurs at 70 wt % of genistein. This observation combined with the larger isotropic composition range for PVP/genistein blends suggests that genistein is also seemingly more miscible with PVP than with PA. The suppression of Tg of the blends upon genistein may be due to the lower glass transition of genistein (if any exists) compared to that of PVP.

PVP does not self-associate, but contains functional groups (C=O) that are capable of forming hydrogen bonds with genistein via electron donor-acceptor type of interaction.

Figure 23:
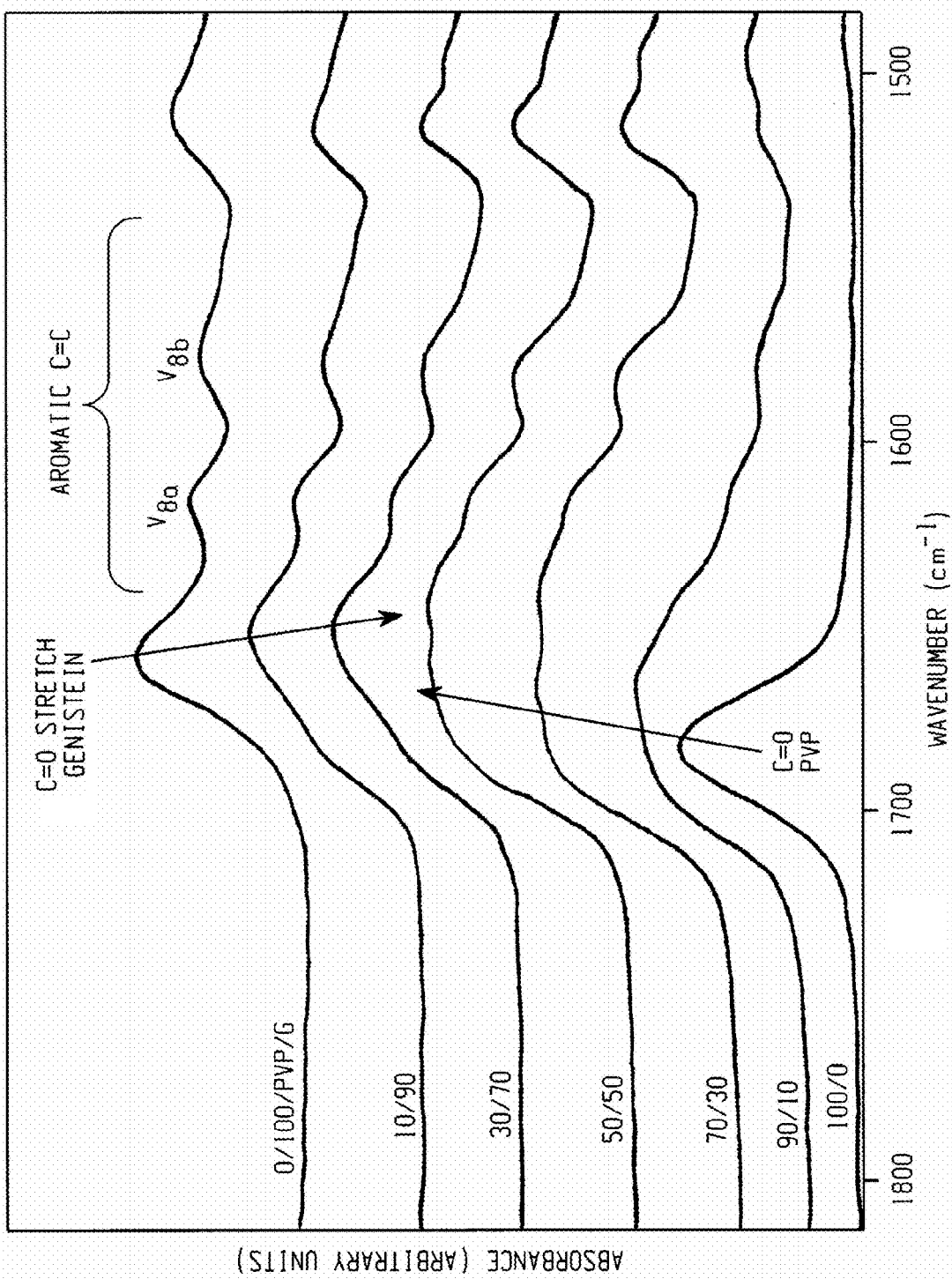
FIGS. 23 and 24 illustrate the FTIR spectrum of PVP/genistein blends in the 1500-1800 and 2800-3600 $cm^{-1}$ range, respectively.
Figure 24:
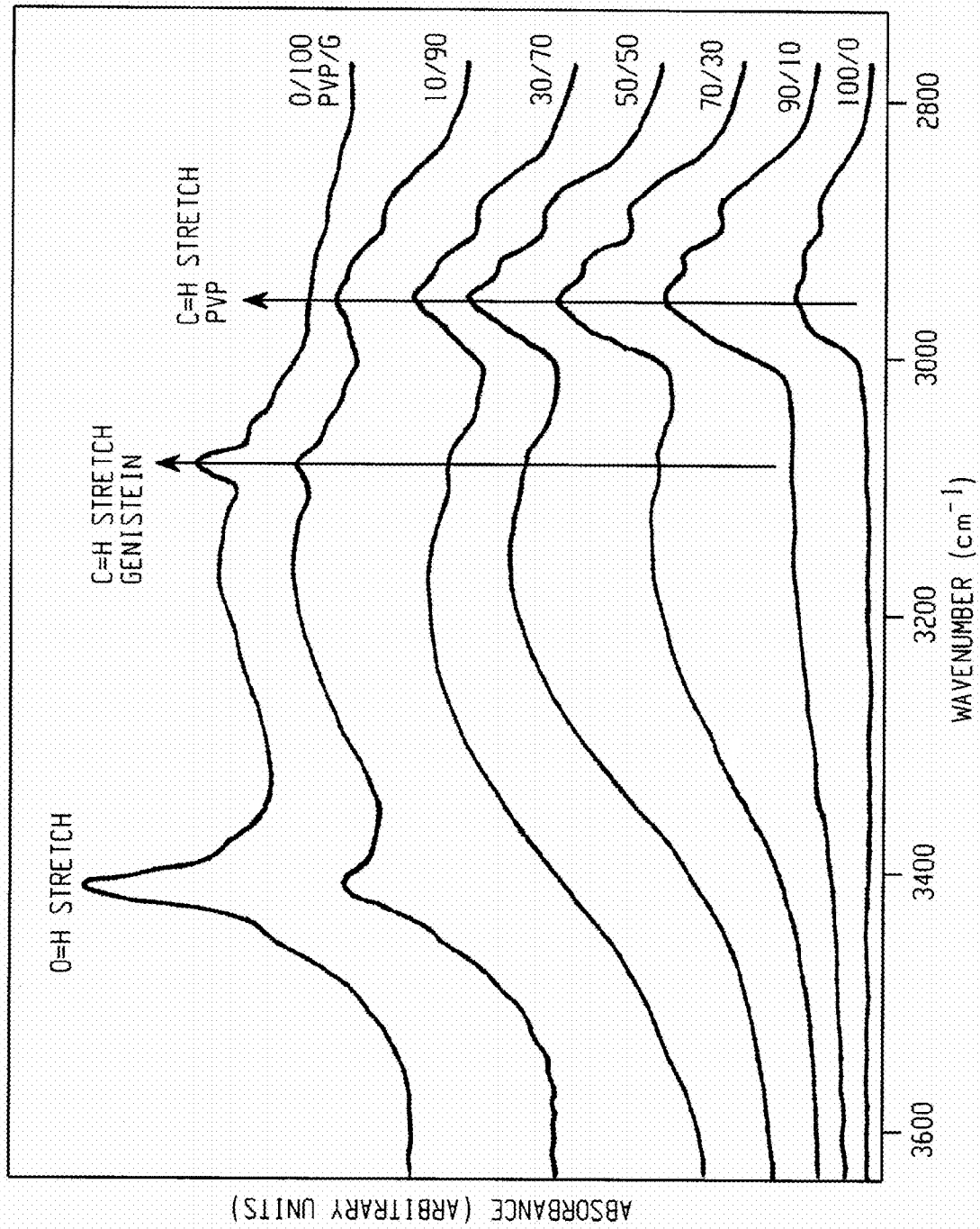

FIGS. 23 and 24 illustrate the FTIR spectrum of PVP/genistein blends in the 1500-1800 and 2800-3600 cm$^{-1}$ range, respectively. These spectra were acquired at 100° C. to minimize moisture absorption. The FTIR analysis of the present PVP/genistein system is relatively straightforward. The FTIR spectra recorded at 100° C. for PVP/genistein blends in the range 1500-1800 cm$^{-1}$ demonstrates hydrogen bonding formation illustrated by the systematic movement of C=O band of the blends to lower frequencies. The aromatic C=C band of genistein does not show any shift. The spectra in the 2800-3600 cm$^{-1}$ range illustrates the broadening of the O—H band upon mixing.

As the concentration of PVP is increased the hydroxyl band becomes broader and shifts to lower frequencies while reducing its magnitude. However, the sharp O—H stretching band of genistein disappears by adding 30 wt % PVP. The corresponding effect can be explicitly seen in the carbonyl spectral region in which the carbonyl peak of PVP shifts to lower frequencies due to hydroxylcarbonyl interactions.

Figure 25:
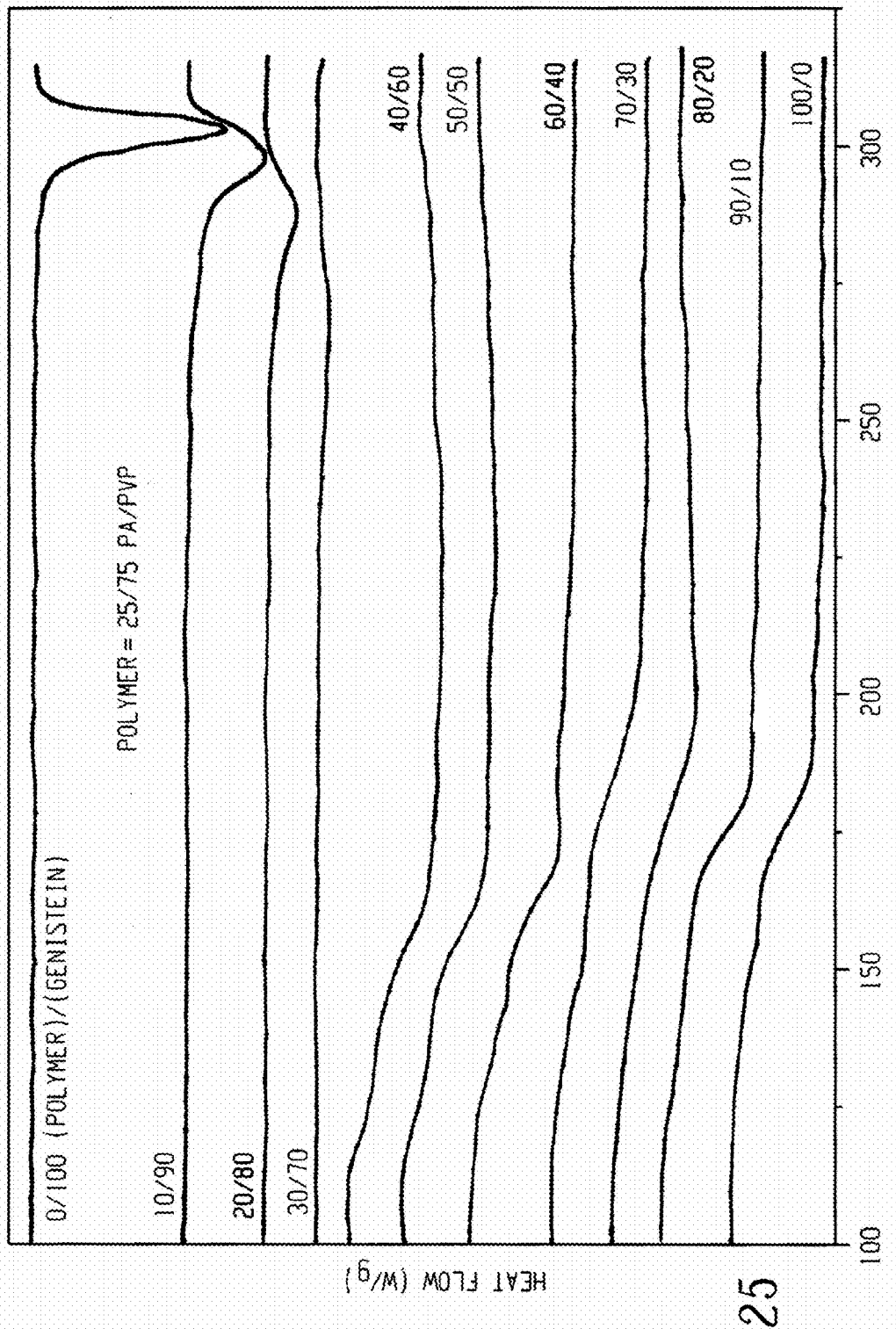
FIGS. 25 and 26 shows second run DSC thermograms for PA/PVP/genistein ternary blends with a 25/75 PA/PVP ratio and 50/50 PA/PVP ratio respectively.
Figure 26:
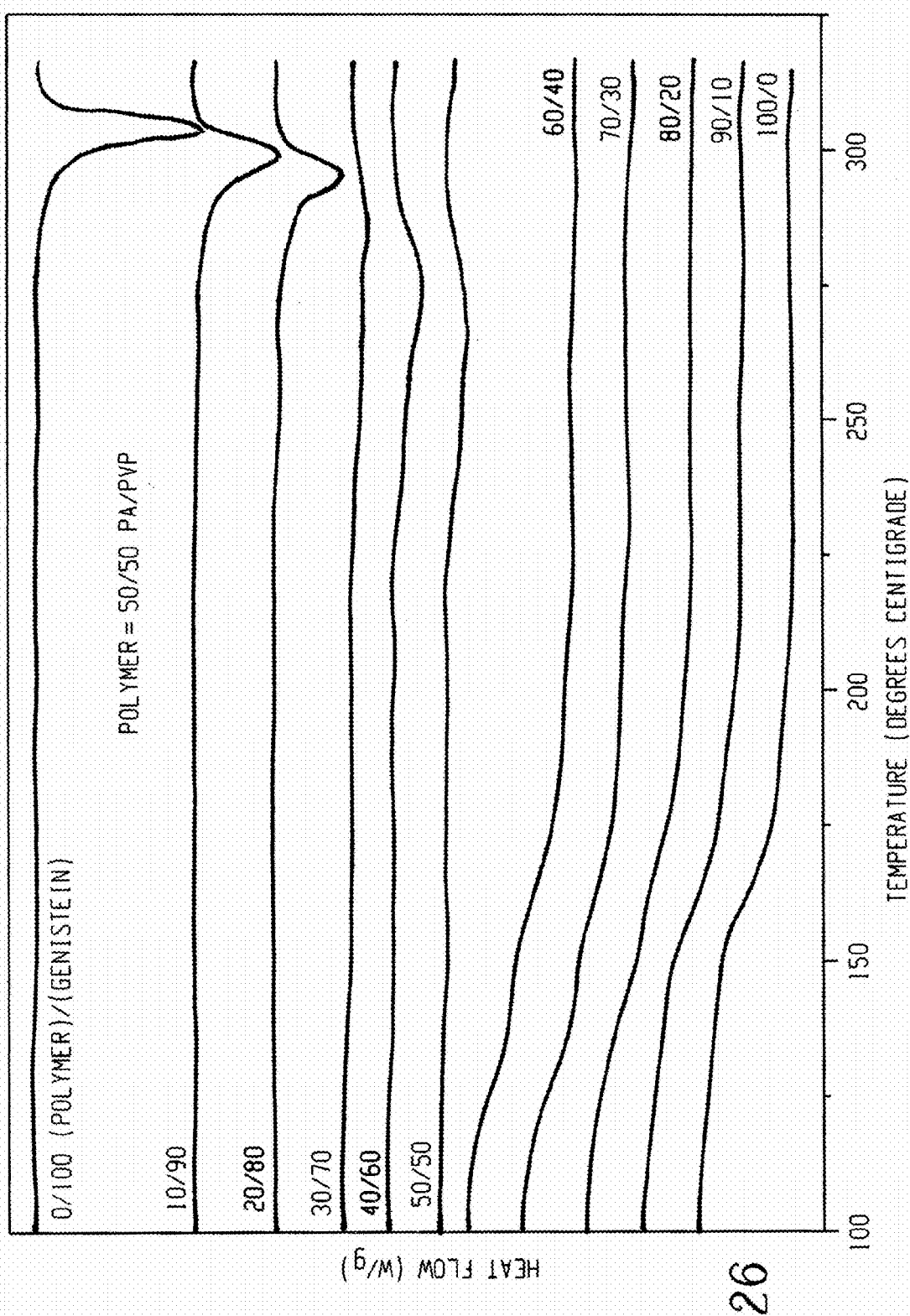

The weaker interaction between PVP and genistein is also manifested in ternary blends. The miscibility behavior of PA/PVP/genistein blends was determined via DSC (FIGS. 25 and 26) and POM experiments. The 25/75 PA/PVP blend exhibits a single $T_g$ at low genistein composition and two $T_g$s at higher genistein compositions, which shift consistently to lower temperature with increase in genistein composition. A 50:50 PA/PVP blend shows a similar trend as 25/75 PA/PVP blends except that liquid-liquid phase separation occurs at even lower genistein compositions.

Upon addition of genistein to the PVP rich-blends (e.g., 25/75 PA/PVP, FIG. 25), a single glass transition is evident up to 30 wt % of genistein. However, beyond 30 wt % dual glass transition temperatures were observed between 40-60 wt % of genistein suggesting phase separation. Further, the $T_9$ of both the phases shifted to lower temperature which was different from the mangiferin system. In the case of 50/50 PA/PVP blends (FIG. 26), liquid-liquid phase separation occurred at even lower concentration (20 wt. %) and this phase separated trend continues with further increase of genistein concentration in which the dual glass transitions shining to lower temperatures. A similar trend was observed for when genistein was added to 75/25 PA/PVP system (data not shown). The phenomena of liquid-liquid phase separation and solid-liquid phase transition can be confirmed by an independent approach such as POM. The PA/genistein and PVP/genistein blends were transparent to the naked eye showing no indication of liquid-liquid phase separation at low genistein loading. Increase in genistein concentration resulted in crystallization of genistein showing the large spherulitic structures in the continuum of isotropic liquid signifying the isotropic-crystal (liquid-solid) coexistence phase. At high concentrations of genistein, the entire field of optical microscope view was filled with solid crystals. In the case of PA/PVP blends, the addition of genistein revealed liquid-liquid phase separated domains in addition to isotropic single phase and crystal+liquid coexistence phase.

Figure 27:
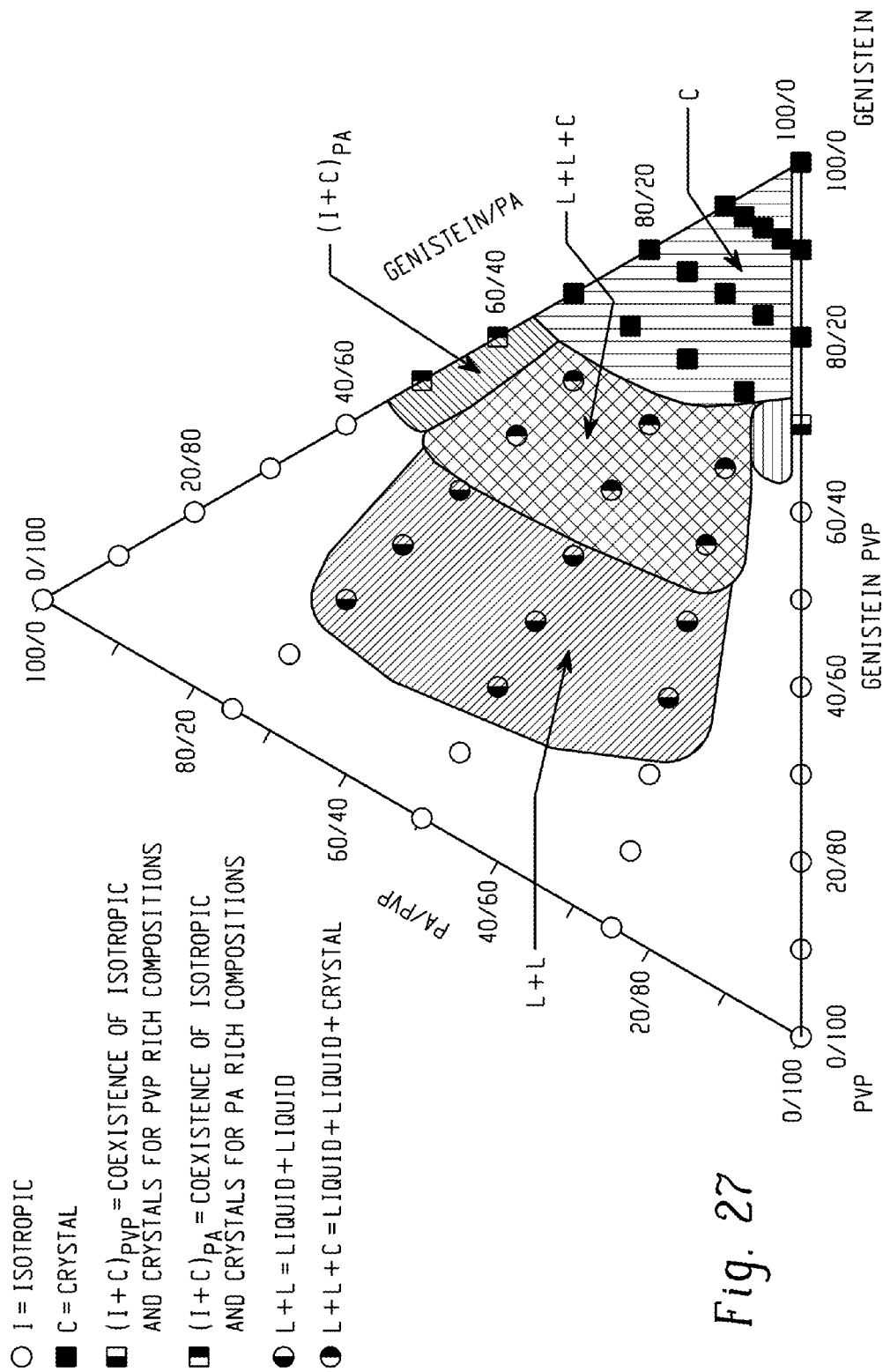
FIG. 27 shows a ternary morphology phase diagram, mapped out with the DSC and optical microscope data for the PA/PVP/genistein blends, showing various coexistence regions.

The DSC and POM data were utilized in order to construct a ternary phase diagram of PA/PVP/genistein system, as shown in FIG. 27. Polarized and unpolarized optical microscope images representing typical morphology of each region are shown in relation to the ternary phase diagram.

The ternary phase diagrams were generated at different concentrations to demonstrate miscibility. The diagrams show that there are isotropic, liquid-liquid, liquid-liquid plus crystal, isotropic plus crystal and crystal phase separation regions, depending on the concentration ratios. The isotropic phase indicates that the composition has the same properties in all directions. The liquid-liquid phase is a phase separated structure in which one phase contains PA with some dissolved quantity of genistein and the other phase contains PVP with some dissolved quantity of genistein. The fluids can freely form a distinct surface at the boundaries of its bulk material. The crystal phase is a solid in which the constituent atoms, molecules or ions are packed in a regularly ordered, repeating pattern extending in all three spatial dimensions.

Summary of Exemplary Results

It has been demonstrated that a soybean-derived phytochemical, genistein, can be incorporated into poly(amide):poly(vinyl pyrrolidone) (PA:PVP) and PES:PVP blends for application as functional hemodialysis membranes. The membranes are shown to be non-cytotoxic to the PBMC. Such membranes are able to reduce reactive oxygen species (ROS), and to suppress the levels of three clinically relevant cytokines viz., IL-1β, IL-6, and TNF-α. The surface crystallization of genistein at the pore interface may contribute to the improvement of anti-oxidant and anti-inflammability properties of some of these genistein modified membranes.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A dialyzer filter unit comprising a semi-permiable membrane housed within the dialyzer filter unit, the semi-permiable membrane being formed from a biocompatible polymer composition comprising:
   a matrix material; and
   an isoflavone or a flavone at least partially dispersed in the matrix material.

2. The dialyzer filter unit of claim 1, wherein the matrix material is selected from the group consisting of polyamides, polyvinylpyrrolidones, polycarbonates, polysulfones, polyacrylonitriles, and combinations thereof.

3. The dialyzer filter unit of claim 2, wherein the matrix material comprises a polysulfone, the polysulfone comprising a polyethersulfone.

4. The dialyzer filter unit of claim 1, wherein the matrix material comprises a blend comprising a polyvinylpyrrolidone and at least one of a polyamide and a polyethersulfone.

5. The dialyzer filter unit of claim 4, wherein the at least one of a polyamide and a polyethersulfone constitutes at least 5% by weight of the matrix material.

6. The dialyzer filter unit of claim 4, wherein the at least one of a polyamide and a polyethersulfone constitutes at least 40% by weight of the matrix material.

7. The dialyzer filter unit of claim 4, wherein the at least one of a polyamide and a polyethersulfone constitutes up to 95% by weight of the matrix material.

8. The dialyzer filter unit of claim 1, wherein the polymer composition is a solid at a temperature of at least 30° C.

9. The dialyzer filter unit of claim 1, wherein the polymer composition comprises an isoflavone and the isoflavone comprises a hydroxyisoflavone.

10. The dialyzer filter unit of claim 9, wherein the hydroxyisoflavone has a structure represented by Structure I:

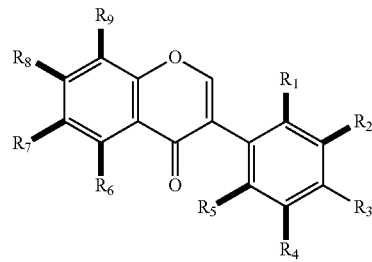

where $R_1$, $R_2$, $R_3$, $R_4$, $R_5$, $R_6$, $R_7$, $R_8$ and $R_9$ are independently selected from H, OH alkoxy, and glycosyl, and at least one of $R_1$, $R_2$, $R_3$, $R_4$, $R_5$, $R_6$, $R_7$, $R_8$ and $R_9$ is an OH.

11. The dialyzer filter unit of claim 10, wherein $R_3$ and at least one of $R_6$, $R_7$, $R_8$ and $R_9$ is an OH.

12. The dialyzer filter unit of claim 9, wherein the hydroxyisoflavone comprises a trihydroxyisoflavone having at least three hydroxyl groups.

13. The dialyzer filter unit of claim 12, wherein at least one of the three hydroxyl groups forms a first phenol ring and another of the three hydroxyl groups forms a second phenol ring.

14. The dialyzer filter unit of claim 10, wherein the hydroxyisoflavone has the structure of Structure II:

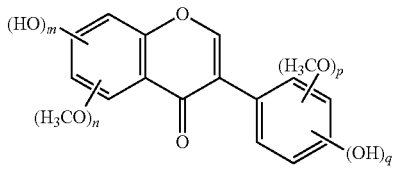

where m, n and p can independently be 0, 1, or 2 and q is 1 or 2.

15. The dialyzer filter unit of claim 14, wherein m is 2.

16. The dialyzer filter unit of claim 14, wherein the hydroxyisoflavone is a 4', 5, 7 hydroxyisoflavone.

17. The dialyzer filter unit of claim 14, wherein the hydroxyisoflavone is selected from the group consisting of genistein, daidzein, glycitein, prunetin, biochanin A, orobol, santal, pratensein, formononetin, and glucosides, 13-glycosides, and alkoxy substituted derivatives thereof, and combinations thereof.

18. The dialyzer filter unit of claim 17, wherein the hydroxyisoflavone is selected from the group consisting of genistein, daidzein, and combinations thereof.

19. The dialyzer filter unit of claim 10, wherein the hydroxyisoflavone is a non-glycosylated hydroxyisoflavone.

20. The dialyzer filter unit of claim 1, wherein the at least one of the isoflavone and flavone constitutes at least 1% by weight of the polymer composition.

21. The dialyzer filter unit of claim 1, wherein at least one of the isoflavone and flavone constitutes at least 10% by weight of the polymer composition.

22. The dialyzer filter unit claim 1, wherein the at least one of the isoflavone and flavone constitutes up to 50% by weight of the polymer composition.

23. The dialyzer filter unit claim 1, wherein the at least one of the isoflavone and flavone is dispersed throughout the matrix material.

24. The dialyzer filter unit of claim 1, wherein the membrane is in the form of at least one of a thin film and fibers.

25. The dialyzer filter unit of claim 1, wherein the membrane comprises a bundle of hollow fibers.

26. The dialyzer filter unit of claim 25, wherein the hollow fibers have a wall thickness of up to 100 μm.

27. A method of forming a dialyzer filter comprising:
forming a semi-permeable membrane from a biocompatible polymer composition comprising a matrix material and an isoflavone or a flavone at least partially dispersed in the matrix material; and
inserting the membrane into a housing of a dialyzer filter unit.

28. A method of filtering a fluid comprising:
filtering a fluid with the dialyzer filter unit of claim 1, whereby at least one of:
a reactive oxygen species in the fluid is reduced, and
a cytokine production in the fluid is suppressed.

29. A method for hemodialysis or hemofiltration comprising contacting blood with a hollow fiber membrane comprising the dialyzer filter unit of claim 1.

30. The method of claim 27, where the forming of the semi-permeable membrane includes the steps of:
combining a matrix material for forming a polymer matrix and at least one of an isoflavone and a flavone to form a mixture; and
solidifying the mixture.

31. The method of claim 30, wherein combining the matrix material and the at least one of the isoflavone and flavone is carried out in the presence of a solvent.

32. The method of claim 31, wherein the solidifying comprises immersing the mixture into a non-solvent.

33. The method of claim 30, wherein the solidifying includes forming fibers from the mixture.

34. The dialyzer filter unit of claim 9, wherein the hydroxyisoflavone has a structure represented by Structure I:

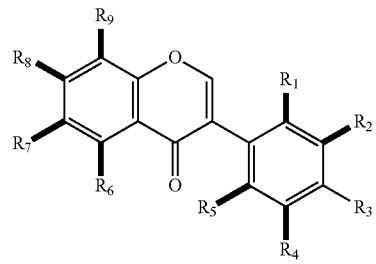

where $R_1$, $R_2$, $R_3$, $R_4$, $R_5$, $R_6$, $R_7$, $R_8$ and $R_9$ are independently selected from H, OH and alkoxy, and at least one of $R_1$, $R_2$, $R_3$, $R_4$, $R_5$, $R_6$, $R_7$, $R_8$ and $R_9$ is an OH.

* * * * *